US012746380B2

(12) United States Patent
Suematsu et al.

(10) Patent No.: US 12,746,380 B2
(45) Date of Patent: Sep. 29, 2026

(54) POWER SUPPLY DEVICE AND MEDICAL DEVICE

(71) Applicant: FURUKAWA ELECTRIC CO., LTD., Tokyo (JP)

(72) Inventors: Katsuki Suematsu, Tokyo (JP); Atsushi Himura, Tokyo (JP); Takeshi Yagi, Tokyo (JP); Kazutaka Nara, Tokyo (JP); Shusuke Kaya, Tokyo (JP); Tsunenori Arai, Tokyo (JP)

(73) Assignee: FURUKAWA ELECTRIC CO., LTD., Tokyo (JP)

(*) Notice: Subject to any disclaimer, the term of this patent is extended or adjusted under 35 U.S.C. 154(b) by 863 days.

(21) Appl. No.: 18/002,900

(22) PCT Filed: Aug. 18, 2021

(86) PCT No.: PCT/JP2021/030173
§ 371 (c)(1),
(2) Date: Dec. 22, 2022

(87) PCT Pub. No.: WO2022/044911
PCT Pub. Date: Mar. 3, 2022

(65) Prior Publication Data
US 2023/0264007 A1 Aug. 24, 2023

(30) Foreign Application Priority Data
Aug. 28, 2020 (JP) ................................ 2020-144262

(51) Int. Cl.
*A61M 39/02* (2006.01)
*A61M 39/00* (2006.01)
*H02J 50/10* (2016.01)

(52) U.S. Cl.
CPC ......... *A61M 39/0208* (2013.01); *H02J 50/10* (2016.02); *A61M 2039/0036* (2013.01);
(Continued)

(58) Field of Classification Search
CPC ...... A61M 39/0208; A61M 2039/0036; A61M 2039/0205; A61M 2205/8243; H02J 50/10
See application file for complete search history.

(56) References Cited

U.S. PATENT DOCUMENTS 4,804,054 A * 2/1989 Howson ............ A61M 39/0208 604/48
5,009,644 A 4/1991 McDonald
(Continued)

FOREIGN PATENT DOCUMENTS

CN 113784739 A 12/2021
EP 0 410 734 A1 1/1991
(Continued)

OTHER PUBLICATIONS

International Search Report issued Oct. 19, 2021 in PCT/JP2021/030173, filed on Aug. 18, 2021, 3 pages.
(Continued)

*Primary Examiner* — Cris L. Rodriguez
(74) *Attorney, Agent, or Firm* — Oblon, McClelland, Maier & Neustadt, L.L.P.

(57) ABSTRACT

A power supply device includes a power transmission coil which supplies electric power from outside the body in a non-contact manner via a power reception coil of an intracorporeal implanting-type medical appliance to which a drug solution is injected from outside the body. A support supports the power transmission coil, and an adhesive part is formed on the side of the support facing the body surface of a living subject.

13 Claims, 23 Drawing Sheets

(52) U.S. Cl.
CPC ............... *A61M 2039/0205* (2013.01); *A61M 2205/8243* (2013.01)

(56) References Cited

U.S. PATENT DOCUMENTS

| | | | | |
|---|---|---|---|---|
| 5,171,228 | A | 12/1992 | McDonald | |
| 5,620,419 | A * | 4/1997 | Lui | A61M 39/0208 604/116 |
| 6,275,737 | B1 * | 8/2001 | Mann | A61N 1/37235 607/61 |
| 10,707,692 | B2 * | 7/2020 | Schmidt | A61B 5/0031 |
| 11,191,973 | B2 * | 12/2021 | Escalona | A61M 60/873 |
| 11,766,550 | B2 * | 9/2023 | Mitchell | G16H 10/60 604/288.01 |
| 2004/0199220 | A1 | 10/2004 | Cantlon | |
| 2008/0303480 | A1 * | 12/2008 | Prutchi | H02J 50/90 320/108 |
| 2013/0150936 | A1 | 6/2013 | Takahashi | |
| 2015/0148665 | A1 | 5/2015 | Sato | |
| 2017/0100056 | A1 * | 4/2017 | Zhu | H02J 50/10 |
| 2017/0100598 | A1 * | 4/2017 | Gross | A61N 1/3787 |
| 2018/0154074 | A1 | 6/2018 | Blomme et al. | |
| 2018/0200412 | A1 * | 7/2018 | Dang | A61K 31/727 |
| 2020/0061337 | A1 | 2/2020 | Singh et al. | |
| 2022/0040404 | A1 | 2/2022 | Suematsu et al. | |

FOREIGN PATENT DOCUMENTS

| | | | | |
|---|---|---|---|---|
| EP | 1882484 | A2 * | 1/2008 | A61N 1/37223 |
| EP | 3 967 339 | A1 | 3/2022 | |
| JP | 3-90168 | A | 4/1991 | |
| JP | 2005349061 | A * | 12/2005 | |
| JP | 2013-123484 | A | 6/2013 | |
| JP | 5958922 | B2 | 8/2016 | |
| JP | 2018-501021 | A | 1/2018 | |
| WO | WO 2016/112401 | A1 | 7/2016 | |
| WO | WO-2019163988 | A1 * | 8/2019 | H02J 50/10 |
| WO | WO 2020/226059 | A1 | 11/2020 | |

OTHER PUBLICATIONS

Extended European Search Report issued Aug. 21, 2024 in European Patent Application No. 21861339.6, 8 pages.
Combined Chinese Office Action and Search Report issued on Jun. 28, 2023 in Chinese Patent Application No. 202180008608.7 (with English translation), 31 pages.

* cited by examiner

POWER SUPPLY DEVICE AND MEDICAL DEVICE

TECHNICAL FIELD

The present invention pertains to a power supply device that supplies power to an intracorporeal implant-type medical appliance into which a drug solution is injected from outside the body, and a medical device provided with this power supply device.

BACKGROUND ART

A medical device provided with an intracorporeal implant-type medical appliance, the main body section of which is implanted inside a body, is used in order to supply a drug solution into the body. This medical appliance is for reducing the load on a patient who must frequently undergo intravenous injections in order to be supplied with the drug solution. For example, Patent Document 1 describes this type of technology. A medical appliance described in Patent Document 1 has a soft section through which an injection needle is inserted into a main body section. This soft section is formed from silicone rubber, for example. In the medical appliance, a drug solution is injected through the soft section into a drug solution container. The drug solution is transported into a blood vessel through a catheter.

Patent Document 1: Japanese Patent No. 5958922

DISCLOSURE OF THE INVENTION

Problems to be Solved by the Invention

Incidentally, in a case of desiring to use a power supply device to supply electric power in a non-contact manner from outside the body to a medical appliance implanted into a body, in order to supply the electric power in a non-contact manner, it is necessary for the power supply device to get closer to a portion in the medical appliance which is to be supplied with power, until the distance therebetween enables power to be supplied. For example, it can be considered that a user would use their hand to hold the power supply device at a position where supply of power to the medical appliance is possible, but performing puncturing work at the same time as the supply of power would be difficult.

The present disclosure is made in the light of the above, and an object of the present disclosure is to provide a power supply device that enables a puncturing operation to be easily performed while supplying electric power to an intracorporeal implant-type medical appliance, and to provide a medical device provided with the power supply device.

Means for Solving the Problems

A power supply device according to the present disclosure is provided with: a power transmission coil configured to supply power in a non-contact manner from outside the body via a coil in an intracorporeal implant-type medical appliance configured to be injected with a drug solution from outside the body; a support body configured to support the power transmission coil; and an adhesive section formed on the support body, on a side of the support body that faces a body surface of a living subject.

In the abovementioned disclosure, the power supply device according to the present disclosure is further provided with an elastic deformation section disposed between the support body and the adhesive section, the elastic deformation section being deformable.

In the abovementioned disclosure, in the power supply device according to the present disclosure, the support body and the adhesive section have been subjected to sterilization treatment.

In the abovementioned disclosure, in the power supply device according to the present disclosure, the support body has a hole through which an injection needle for injecting the drug solution can be inserted, and the power transmission coil is disposed so as to surround the hole.

In the abovementioned disclosure, in the power supply device according to the present disclosure, the power transmission coil is provided with a connector between conductors that configure coils of the power transmission coil.

In the abovementioned disclosure, in the power supply device according to the present disclosure, the support body has a cutout section that has been cut out such that an injection needle for injecting the drug solution can be inserted through the cutout section, and the power transmission coil is formed in alignment with a shape of the cutout section.

In the abovementioned disclosure, in the power supply device according to the present disclosure, the power transmission coil is formed into a spiral.

In the aforementioned disclosure, a medical device according to the present disclosure is provided with: the power supply device; and an intracorporeal implant-type medical appliance, in which the medical appliance is provided with a soft section through which an injection needle for injecting a drug solution can be inserted, a drug solution container having an opening occluded by the soft section and being configured to receive the drug solution injected from the injection needle, and a power reception section configured to use a coil to receive, in a non-contact manner, power supplied from the power transmission coil in the power supply device.

In the aforementioned disclosure, in the medical device according to the present disclosure, the medical appliance is further provided with a light-emitting section configured to emit light.

In the aforementioned disclosure, a medical device according to the present disclosure is provided with: the power supply device; and an intracorporeal implant-type medical appliance, wherein the medical appliance is provided with a soft section through which an injection needle for injecting a drug solution can be inserted, a drug solution container having an opening occluded by the soft section and being configured to receive the drug solution injected from the injection needle, a power reception section configured to use a coil to receive, in a non-contact manner, power supplied from the power transmission coil in the power supply device, and a light-emitting section configured to emit light, in which a diameter of the hole in the power supply device is greater than an outer diameter of the soft section, and a radius of the hole is greater than the distance between the center of the soft section and the light-emitting section in a plan view.

Effects of the Invention

By virtue of the present invention, it is possible to provide a power supply device that enables a puncturing operation to be easily performed while supplying electric power to an intracorporeal implant-type medical appliance, and to provide a medical device provided with the power supply device.

PREFERRED MODE FOR CARRYING OUT THE INVENTION

Embodiments for working the present disclosure are, together with the drawings, described in detail below. Note that the present disclosure is not limited by the following embodiments. In addition, each drawing referred to in the following description merely schematically illustrates shapes, sizes, and positional relationships to a degree that enables the content of the present disclosure to be understood. In other words, the present disclosure is not limited to only the shapes, sizes, and positional relationships exemplified in each drawing. Furthermore, in the following description, description is given in detail regarding a medical device that detects a predetermined location in a medical appliance used by being implanted within the body of a living subject, including people and animals, and a power supply device.

First Embodiment

[Configuration of Medical Device]

Figure 1:
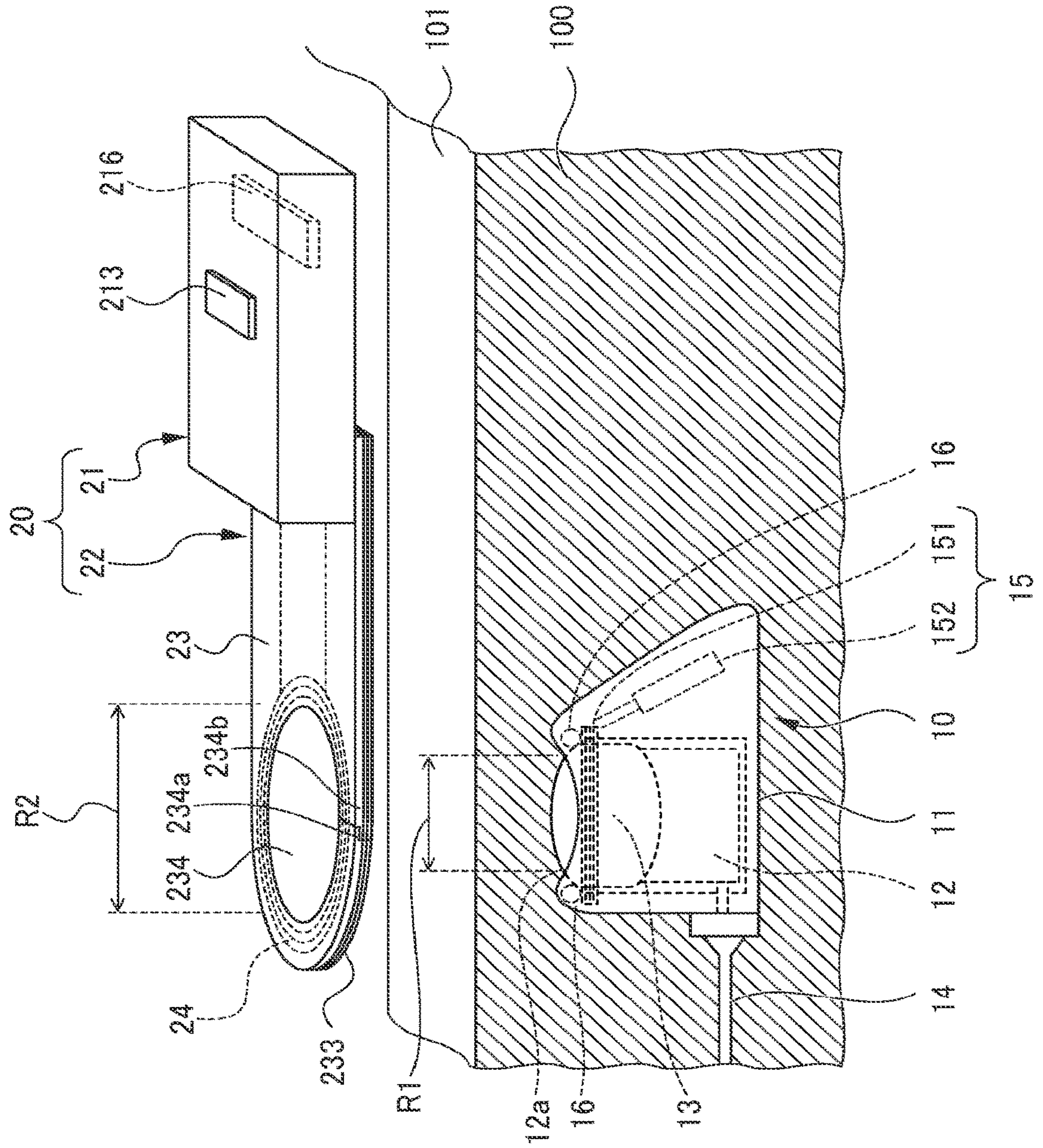
FIG. 1 is a schematic view illustrating an approximate configuration of a medical device according to a first embodiment of the present disclosure.
Figure 2:
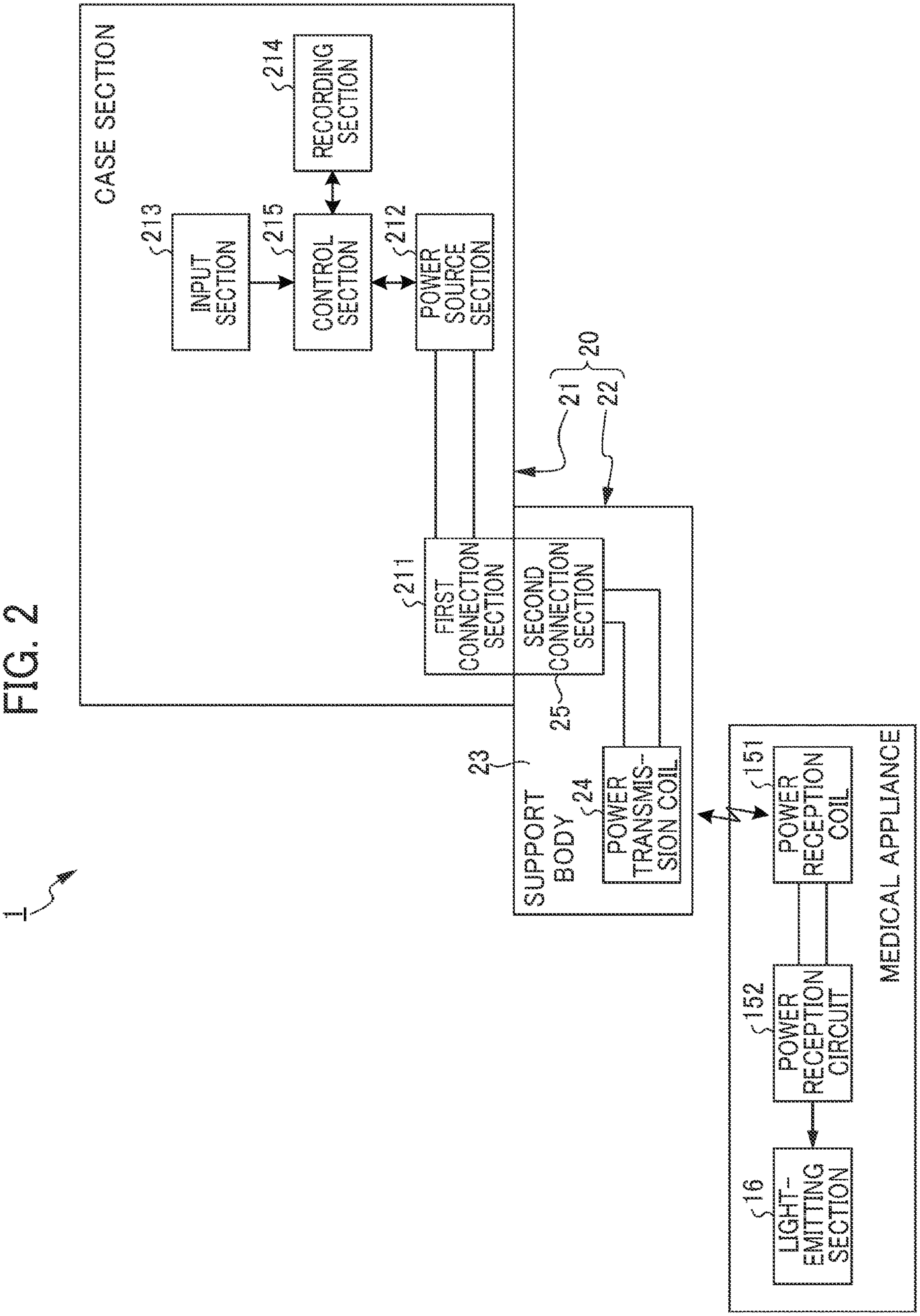
FIG. 2 is a block view illustrating a functional configuration of the medical device according to the first embodiment of the present disclosure.

FIG. 1 is a schematic view illustrating an approximate configuration of a medical device 1 according to the first embodiment. FIG. 2 is a block view illustrating a functional configuration of the medical device 1 according to the first embodiment. The medical device 1 illustrated in FIGS. 1 and 2 is used by being implanted inside the body of a living subject 100. The medical device 1 is provided with a medical appliance 10 that is injected with a drug solution through an injection needle that has been inserted, and a power supply device 20 that supplies electric power to the medical appliance 10.

[Configuration of Medical Appliance]

Figure 3:
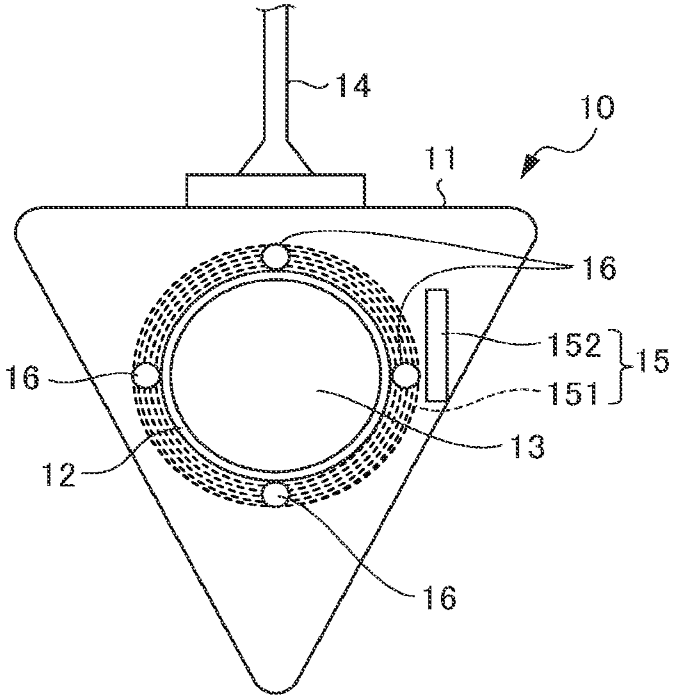
FIG. 3 is a plan view illustrating a medical appliance according to the first embodiment of the present disclosure.

Firstly, a detailed configuration of the medical appliance 10 is described. FIG. 3 is a schematic view illustrating an approximate configuration of the medical appliance 10.

The medical appliance 10 illustrated in FIGS. 1 to 3 is, for example, referred to as a subcutaneous implant-type central venous access port (CV port). As illustrated in FIGS. 1 to 3, the medical appliance 10 is used with a main body section 11 thereof implanted within the body of the living subject 100.

The main body section 11 is a case made from an epoxy resin, for example. As illustrated in FIGS. 1 to 3, the main body section 11 is provided with a drug solution container 12, a soft section 13, a catheter 14, a power reception section 15, and light-emitting sections 16.

The drug solution container 12 is a location through which an injected drug solution passes, in a transient manner, while being delivered to the catheter. In other words, the drug solution container 12 receives a drug solution injected from an injection needle. The drug solution container 12 has, on an outer side thereof, an opening 12*a* that forms a circle.

The soft section 13 is referred to as a so-called septum. The soft section 13 occludes the opening 12*a* in the drug solution container 12. The soft section 13 is a soft lid body (silicone plug) made from silicone rubber, for example, and is provided in a form that also exposes the main body section 11. The soft section 13 also forms a circular column. The soft section 13 is a portion through which an injection needle for injecting a drug solution from a body surface 101 of the living subject 100 can be inserted, after the main body section 11 is implanted inside the body of the living subject 100.

The soft section 13 may be transparent or opaque. It is desirable for the soft section 13 to be transparent in a case where a light-emitting section 16 described below is disposed at the bottom surface of the drug solution container 12. In a case of disposing a light-emitting section 16 at the bottom surface of the drug solution container 12, it is desirable for the transmittance of the soft section 13 to be at least 90% for the wavelength of light emitted by the light-emitting section 16.

One end of the catheter 14 is in communication with the drug solution container 12, and the other end of the catheter 14 is inserted into, for example, a blood vessel (not illustrated). The catheter 14 communicates with the drug solution container 12 and transports a drug solution to the blood vessel.

The power reception section 15 is configured to receive electric power in a non-contact manner from a later-described power transmission coil 24 belonging to the power supply device 20. The power reception section 15 is provided with a power reception coil 151 and a power reception circuit 152.

The power reception coil 151 is formed by being wound a plurality of times into an annular shape around the end surface on the outer side of the drug solution container 12, and is provided at the periphery of the soft section 13. The power reception coil 151 is primarily configured from copper wire in order to increase power supplied while having a small size, but may be configured from aluminum wire in order to reduce the weight of the power reception coil 151. For example, the power reception coil 151 is formed so as to be approximately 5 g. The power reception coil 151 is obtained in an aspect that is integrated with the main body section 11 by being formed using molding.

The power reception circuit 152 receives electric power (induced electromotive force) generated in the power reception coil 151, and outputs this received electric power to the light-emitting sections 16.

In the present embodiment, the power reception coil 151 in the power reception section 15 is provided so as to surround the soft section 13, but the power reception coil 151 may be wound around a cylindrical iron core having a small diameter. As a result, it is possible to manufacture the power reception section 15 without depending on the magnitude of the outer diameter of the soft section 13 or the shape of the soft section 13.

Figure 4:
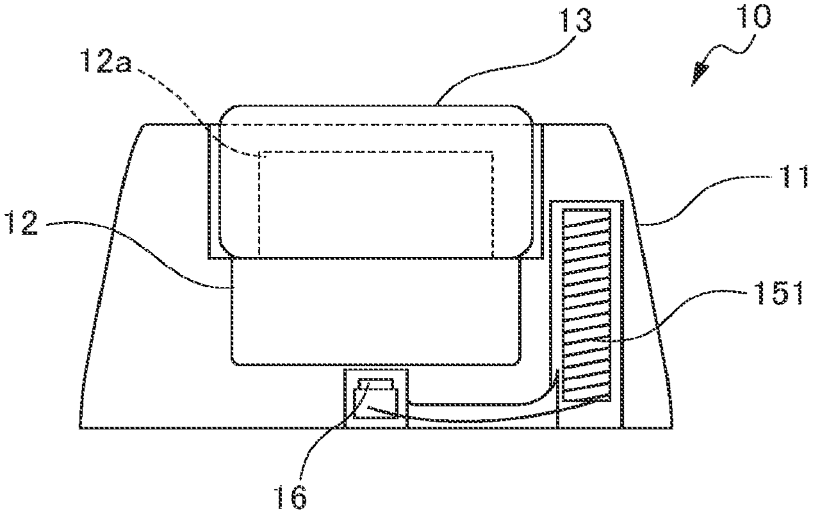
FIG. 4 is a schematic view illustrating a first modification of the medical appliance according to the first embodiment of the present disclosure.
Figure 5:
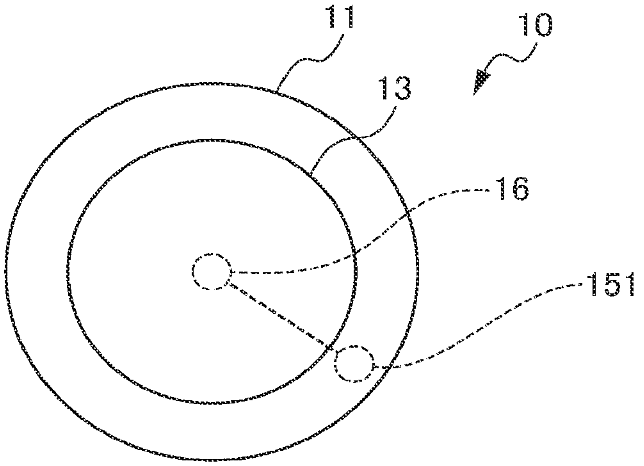
FIG. 5 is a plan view illustrating the first modification of the medical appliance according to the first embodiment of the present disclosure.
Figure 6:
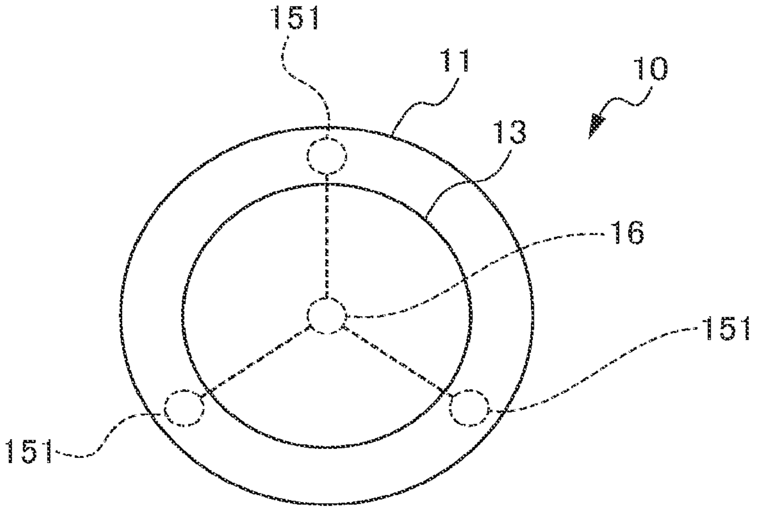
FIG. 6 is a plan view illustrating a second modification of the medical appliance according to the first embodiment of the present disclosure.

FIG. 4 is a schematic view illustrating a first modification of the medical appliance 10. FIG. 5 is a plan view illustrating the first modification of the medical appliance 10. FIG. 6 is a plan view illustrating a second modification of the medical appliance 10. Note that FIGS. 4 to 6 omit illustration of the power reception circuit 152. As illustrated in FIG. 4, the medical appliance 10 may have a configuration in which one light-emitting section 16 is disposed at the bottom surface of the drug solution container 12. In the case of this configuration, for example one or a plurality of the power reception coil 151 (FIG. 6 illustrates an example in which configuration is made with three power reception coils 151) are disposed at the periphery of the drug solution container 12, and are connected to the light-emitting section 16. A groove, through which runs a connection line that connects the power reception coil 151 and the light-emitting section 16, is formed in the main body section 11. Configuration may be such that there is one power reception coil 151 as illustrated in FIG. 5, or a plurality (for example, three) of the power reception coils 151 as illustrated in FIG. 6.

Each light-emitting section 16 is, for example, a light-emitting diode (LED), and emits light in accordance with power received by the power reception circuit 152. Each light-emitting section 16 is disposed at the periphery of the soft section 13, and irradiates at least the top surface of the soft section 13. For example, light-emitting sections 16 are disposed in an annular shape at predetermined intervals at the periphery of the soft section 13. In the present embodiment, light-emitting sections 16 are disposed in an annular shape at approximately 90-degree intervals, at four locations at the periphery of the soft section 13.

The number of light-emitting sections 16 and the disposition thereof can be changed, as appropriate. In other words, there may be three or less light-emitting sections 16, or five or more light-emitting sections 16. In addition, the light-emitting sections 16 may be disposed at a side surface or the bottom surface of the drug solution container 12. For example, there may be a configuration in which at least one light-emitting section 16 is disposed at the center of the bottom surface of the drug solution container 12. In addition, there may be a configuration in which two light-emitting sections 16 are disposed at positions facing each other at the periphery of the soft section 13. By virtue of this configuration in which two light-emitting sections 16 are disposed at facing positions, the center of two points on the body surface 101 illuminated by light L emitted from each light-emitting section 16 indicates the approximate center of the soft section 13, and thus it is possible to specify the center of the soft section 13 while using the light L as a guide. It is desirable for the number of light-emitting sections 16 to be two from the trade-off between the effect of minimizing the number of components and the effect of notifying the position of the soft section 13.

In the present embodiment, the medical appliance 10 has a configuration in which power is supplied from one power reception section 15 to a plurality of light-emitting sections 16. However, in a case where a plurality of light-emitting sections 16 are provided, the medical appliance 10 may have a configuration in which a plurality of power reception sections 15 are disposed and one power reception section 15 is disposed for each light-emitting section 16. In other words, the medical appliance 10 may have a configuration in which one power reception coil 151 and one power reception circuit 152 are provided for one light-emitting section 16. As a result, it is possible to cause each of the plurality of light-emitting sections 16 to emit light independently.

It is desirable for each light-emitting section 16 to use an LED having high directivity. More specifically, it is desirable for the light-emitting section 16 to use a red LED that emits light in the red wavelength band, in order to transmit through a living body such as a living subject.

[Configuration of Power Supply Device]

Figure 7:
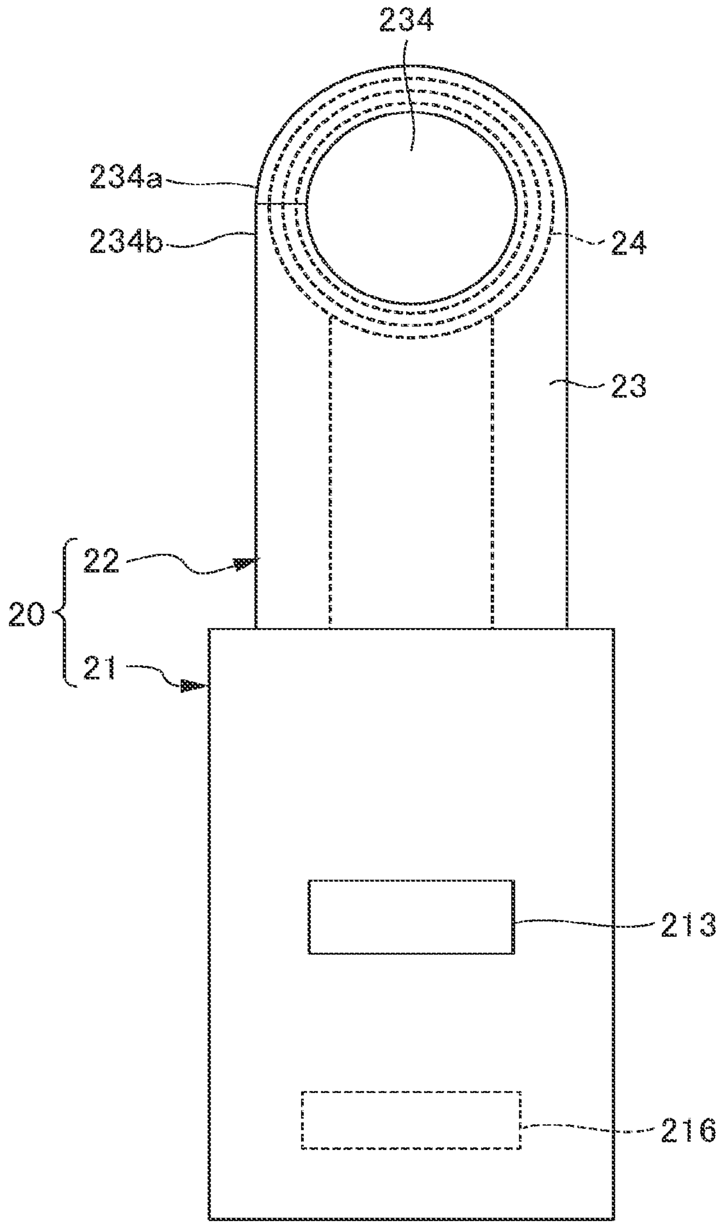
FIG. 7 is a plan view illustrating a power supply device according to the first embodiment of the present disclosure.

Next, description is given regarding an approximate configuration of the power supply device 20. FIG. 7 is a plan view of the power supply device 20.

The power supply device 20 supplies electric power to the intracorporeal implant-type medical appliance 10. As illustrated in FIGS. 1, 2, and 7, the power supply device 20 is provided with a case section 21, and a power transmission section 22 that can be detached from and attached to the case section 21. Note that that case section 21 and the power transmission section 22 may be integrally formed.

[Configuration of Case Section]

Firstly, description is given regarding a configuration of the case section 21. The case section 21 internally houses a circuit board on which is installed a later-described power source, an IC chip, etc. The case section 21 supplies electric power to the power transmission section 22. The case section 21 is provided with a first connection section 211, a power source section 212, an input section 213, a recording section 214, and a control section 215.

The first connection section 211 can be electrically connected to the power transmission section 22 which is mounted to the case section 21, and supplies electric power inputted from the power source section 212 to the power transmission section 22. The first connection section 211 is configured using a female type electric coupler, for example.

The power source section 212 supplies electric power to the power transmission section 22 via the first connection section 211, under control by the control section 215. The power source section 212 is configured by including a battery 216 which is a power source, a voltage-boosting circuit, etc.

The input section 213 accepts input of an operation by a user. The input section 213 is realized using, for example, a button, a switch, and a touch panel. Here, a user is one of a doctor, a nurse, a caregiver, and a patient who is a living subject.

The recording section 214 records various types of programs executed by the power supply device 20, as well as information. The recording section 214 is realized using a volatile memory and a non-volatile memory.

The control section 215 controls each section that configures the power supply device 20. When the input section 213 is pressed, the control section 215 controls the power source section 212 to thereby cause power to be supplied to the power transmission section 22 via the first connection section 211. The control section 215 is realized using a memory and a processor having hardware such as a central processing unit (CPU).

[Configuration of Power Transmission Section]

Figure 8:
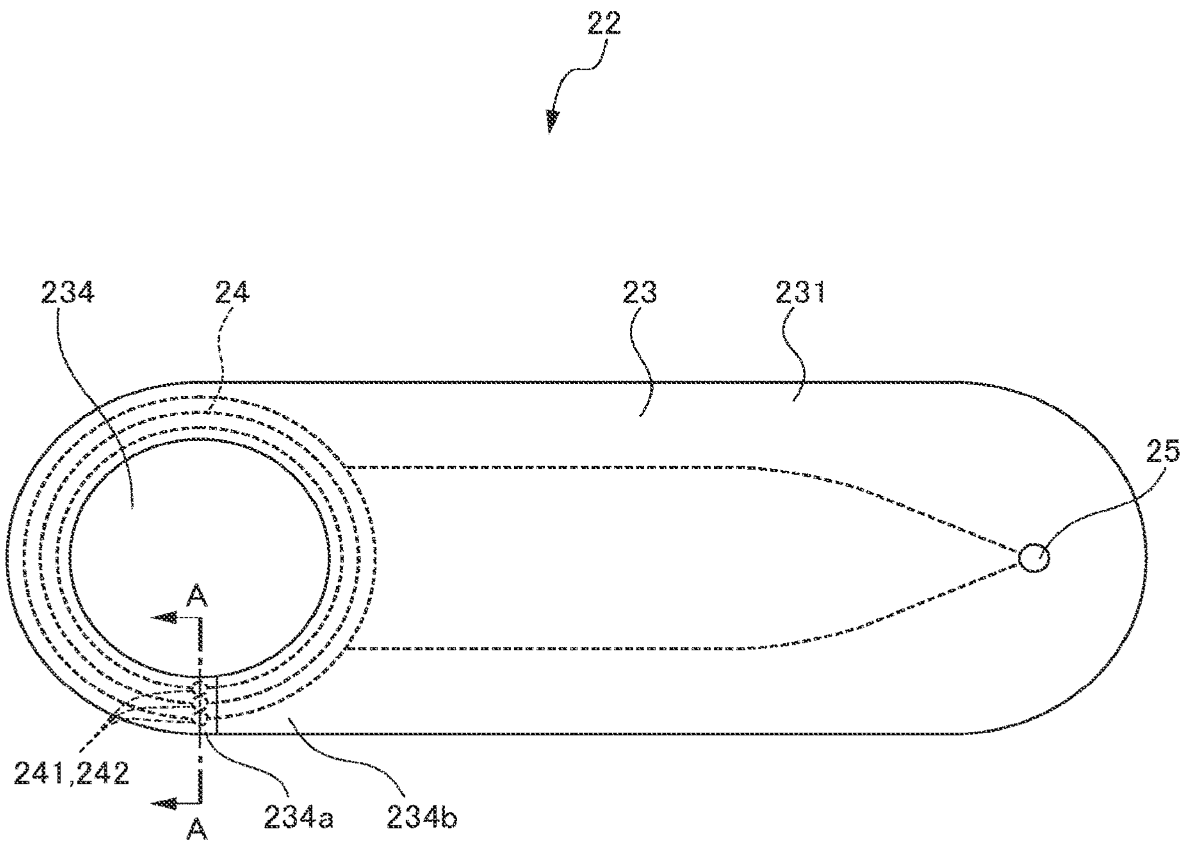
FIG. 8 is a plan view illustrating a power transmission section according to the first embodiment of the present disclosure.
Figure 9:
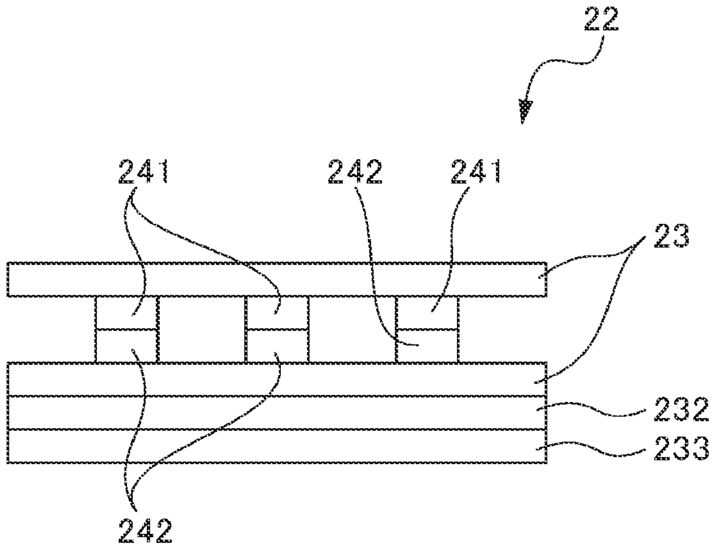
FIG. 9 is a cross-sectional view illustrating the power transmission section according to the first embodiment of the present disclosure.

Next, description is given regarding a configuration of the power transmission section 22. FIG. 8 is a plan view illustrating the power transmission section 22, and FIG. 9 is a cross-sectional view resulting from cutting the power transmission section 22 along an A-A line illustrated in FIG. 8. The power transmission section 22 has functionality for transmitting electric power in a non-contact manner.

As illustrated in FIGS. 1, 2, and 8, the power transmission section 22 has a support body 23, an adhesive section 233, an elastic deformation section 232, the power transmission coil 24, and a second connection section 25. Note that the power transmission section 22 functions as a power transmission sheet in the first embodiment. The support body 23 and the power transmission coil 24 come into contact with the body of a patient. Therefore, it is desirable to not reuse the support body 23 and the power transmission coil 24 from perspectives such as preventing infection. In the present embodiment, the power transmission section 22 and the case section 21 can be attached to and detached from each other. Therefore, it is possible to dispose of the support body 23 and the power transmission coil 24 while keeping the case section 21.

The support body 23 has a long and narrow plate shape. Both ends of the support body 23 in the longitudinal direction are formed as arc shapes. The material of the support body 23 may be non-woven fabric, woven fabric, a resin (a polyethylene (PE) film), or a resin foam (a PE foamed body), for example. The support body 23 supports the power transmission coil 24. In the present embodiment, the support body 23 is formed using two pieces of non-woven fabric that interpose the power transmission coil 24 and the second connection section 25 therebetween.

A hole 234, which is an opening through which an operation to insert an injection needle can be performed, is formed on one side of the support body 23 in the longitudinal direction. In the present embodiment, the hole 234 is configured such that a ring-shaped state is canceled when a first connection end section 234*a* and a second connection end section 234*b*, which overlap, are separated from each other.

It is desirable that an inner diameter R2 of the hole 234 is greater than an outer diameter R1 of the soft section 13, as illustrated in FIG. 1. The inner diameter R2 of the hole 234 is not limited in particular, but it is desirable for the inner diameter R2 to be at least 1 cm. In the present embodiment, the inner diameter R2 of the hole is at least 1 cm. In addition, the radius of the hole 234 is greater than the distance between the center of the soft section 13 and the light-emitting sections 16 in the plan view.

The second connection section 25 is provided at the other side of the support body 23 in the longitudinal direction. The second connection section 25 is electrically connected to the power transmission coil 24 and the power source section 212 in the case section 21. The second connection section 25 is configured using a male electric coupler, for example.

The adhesive section 233 is a layer made from an affixing member, an adhesive member, etc. that can be affixed to the body surface 101 of the living subject 100. As illustrated in FIG. 9, the adhesive section 233 is formed on a side of the support body 23 that faces the body surface 101. In other words, the adhesive section 233 is formed on one surface among from the surfaces of the two pieces of the non-woven fabric, the one surface adapted to come into contact with the body surface 101. The adhesive force exhibited by the adhesive section 233 is desirably 0.9 N/cm to 7.7 N/cm. The thickness of the adhesive section 233 is desirably 25 μm to 100 μm. The material of the adhesive section may be a silicone-based adhesive, for example.

The elastic deformation section 232 is a layer that can deform, has cushioning properties, and is disposed between the support body 23 and the adhesive section 233. The thickness of the elastic deformation section 232 is desirably 1 mm or less. Note that the elastic deformation section 232 is not necessary in a case of following skin with only the support body 23 and the adhesive section 233.

The distance from the core of the power transmission coil 24 to the body surface 101 is desirably within 2 mm. For example, by making the thickness of the elastic deformation section 232 be approximately 1 mm and making the total of the thickness of the support body 23 which comes into contact with the elastic deformation section 232 and the thickness of the adhesive section 233 be 1 mm or less, it is possible to make the distance from the core of the power transmission coil 24 to the body surface 101 be within 2 mm.

The power transmission coil 24 supplies power in a non-contact manner from outside the body via the power reception coil 151 in the intracorporeal implant-type medical appliance 10 which is injected with a drug solution from outside the body. The power transmission coil 24 is a planar coil provided in a ring shape at the periphery of the hole 234. The power transmission coil 24 generates magnetic flux in response to electric power inputted from the case section 21 via the second connection section 25. The power transmission coil 24 is provided with connectors 241 and 242 between conductors that make up the coil. In other words, the power transmission coil 24 is configured such that, from among conductors that make up the power transmission coil 24, the conductors on one side of the power transmission coil 24 and the conductors on the other side of the power transmission coil 24 are connected through the connectors 241 and 242. In the present embodiment, the power transmission coil 24 is configured such that it is possible to release the ring-shaped state using the connectors 241 and 242.

Figure 10A:
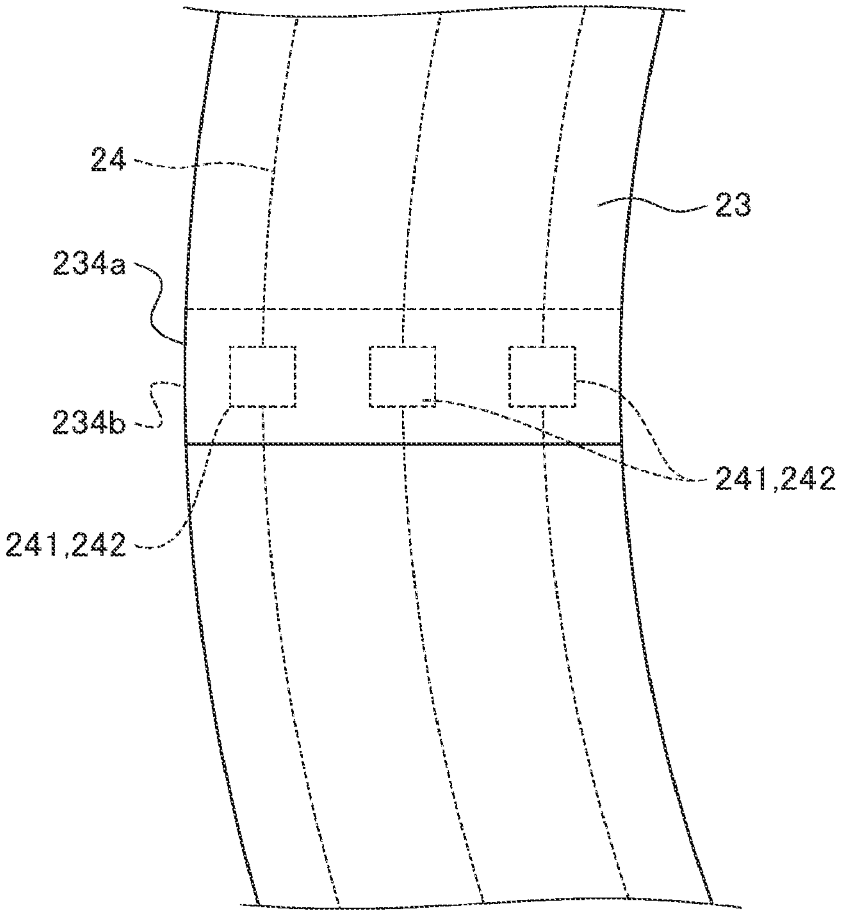
FIG. 10A is an enlarged view illustrating the vicinity of a first connection end section and a second connection end section illustrated in FIG. 8 of a support body in a state where connectors according to the first embodiment of the present disclosure are connected.
Figure 10B:
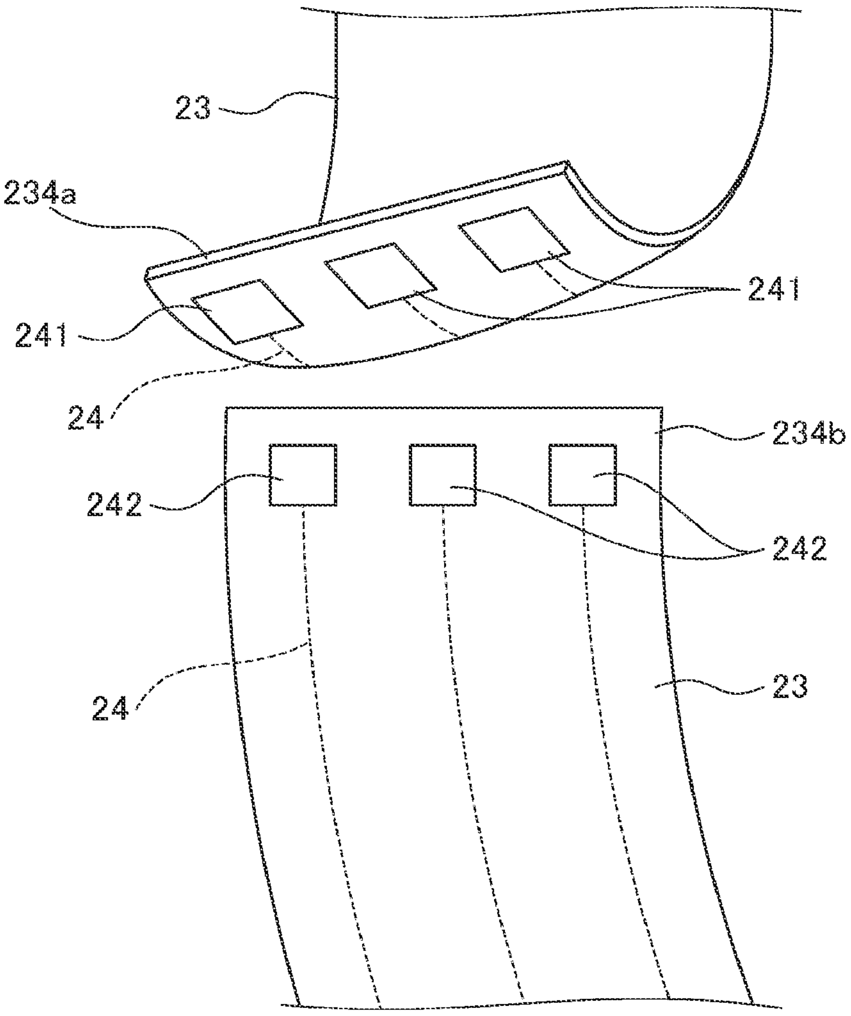
FIG. 10B is an enlarged view illustrating the vicinity of the first connection end section and the second connection end section illustrated in FIG. 8 of the support body in a state where the connections between the connectors according to the first embodiment of the present disclosure have been released.

With reference to FIGS. 10A and 10B, description is given regarding a configuration for releasing the ring-shaped state of the power transmission coil 24. FIG. 10A is an enlarged view of the vicinity of the first connection end section 234*a* and the second connection end section 234*b* of the support body 23 in a state where the connectors 241 and 242 are connected.

FIG. 10B is an enlarged view of the vicinity of the first connection end section 234*a* and the second connection end section 234*b* of the support body 23 in a state where the connections between the connectors 241 and 242 has been released.

The power transmission coil 24 has the connectors 241 and 242. As illustrated in FIGS. 10A and 10B, the connectors 241 are disposed on the first connection end section 234*a* side, and the connectors 242 are disposed on the second connection end section 234*b* side. The connectors 241 and the connectors 242 can be attached to and detached from each other.

As illustrated in FIG. 10A, by connecting the connectors 241 to the top of the connectors 242, the power transmission coil 24 is formed into a ring shape as a whole, the first connection end section 234*a* and the second connection end section 234*b* overlap, and the approximately circular shaped hole 234 is formed in the plan view.

As illustrated in FIG. 10B, by separating the connectors 241 and the connectors 242, the ring-shaped state of the power transmission coil 24 is released, and the first connection end section 234*a* and the second connection end section 234*b* of the support body 23 are separated. As a result, it is possible to use a gap formed by releasing the ring-shaped state of the power transmission coil 24 to remove the power transmission section 22 from the body surface 101 while avoiding coming into contact with an injection needle which is in a state of having punctured the body surface 101.

[Procedure for Supplying Drug Solution into Body of Living Subject 100 Using Medical Device 1]

Figure 11A:
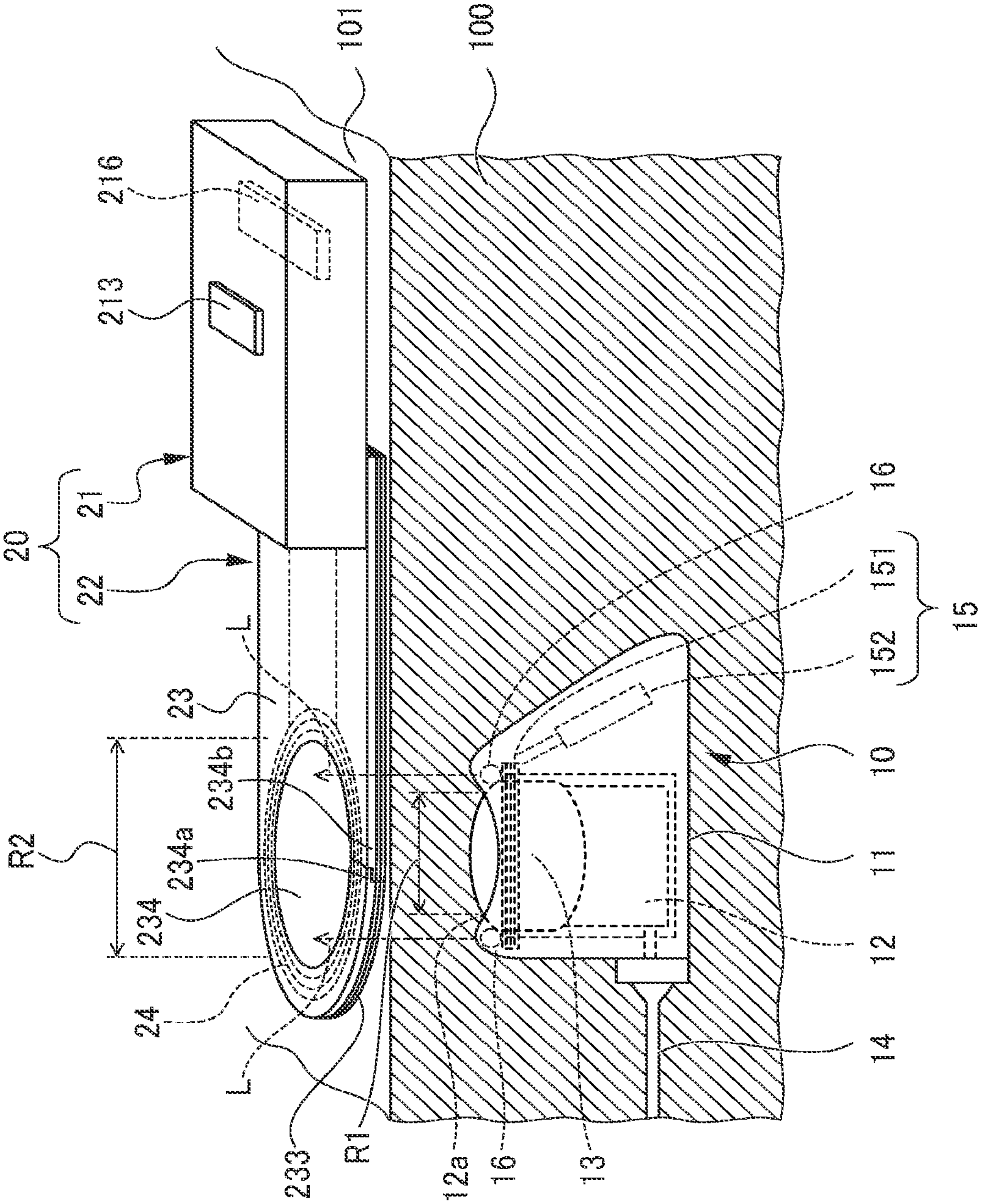
FIG. 11A is a first schematic view illustrating a situation at a stage before using puncturing to supply a drug solution into a living body using the medical device according to the first embodiment of the present disclosure.
Figure 11B:
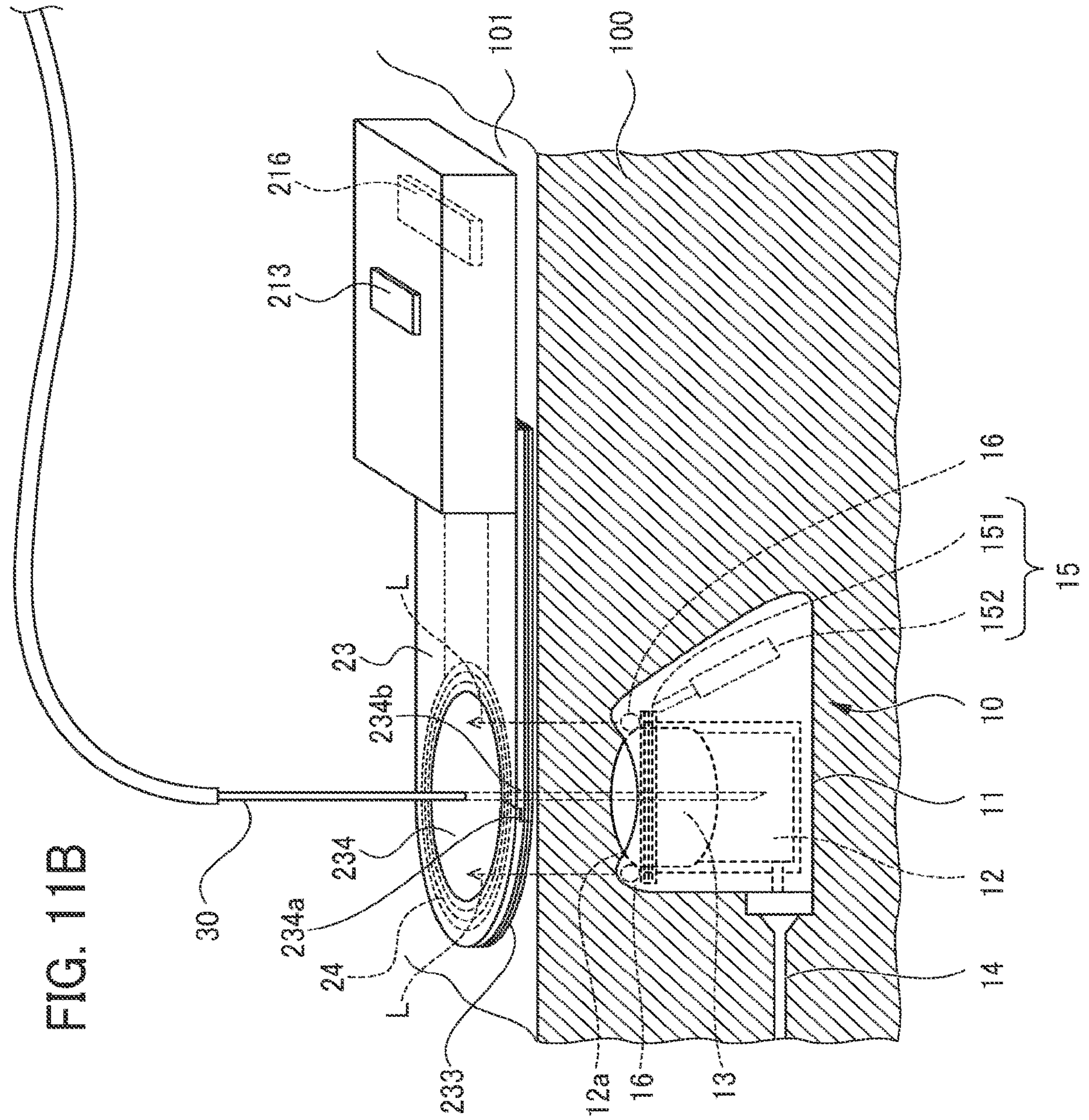
FIG. 11B is a second schematic view illustrating a situation in which the drug solution is supplied into the living body using the medical device according to the first embodiment of the present disclosure.
Figure 11C:
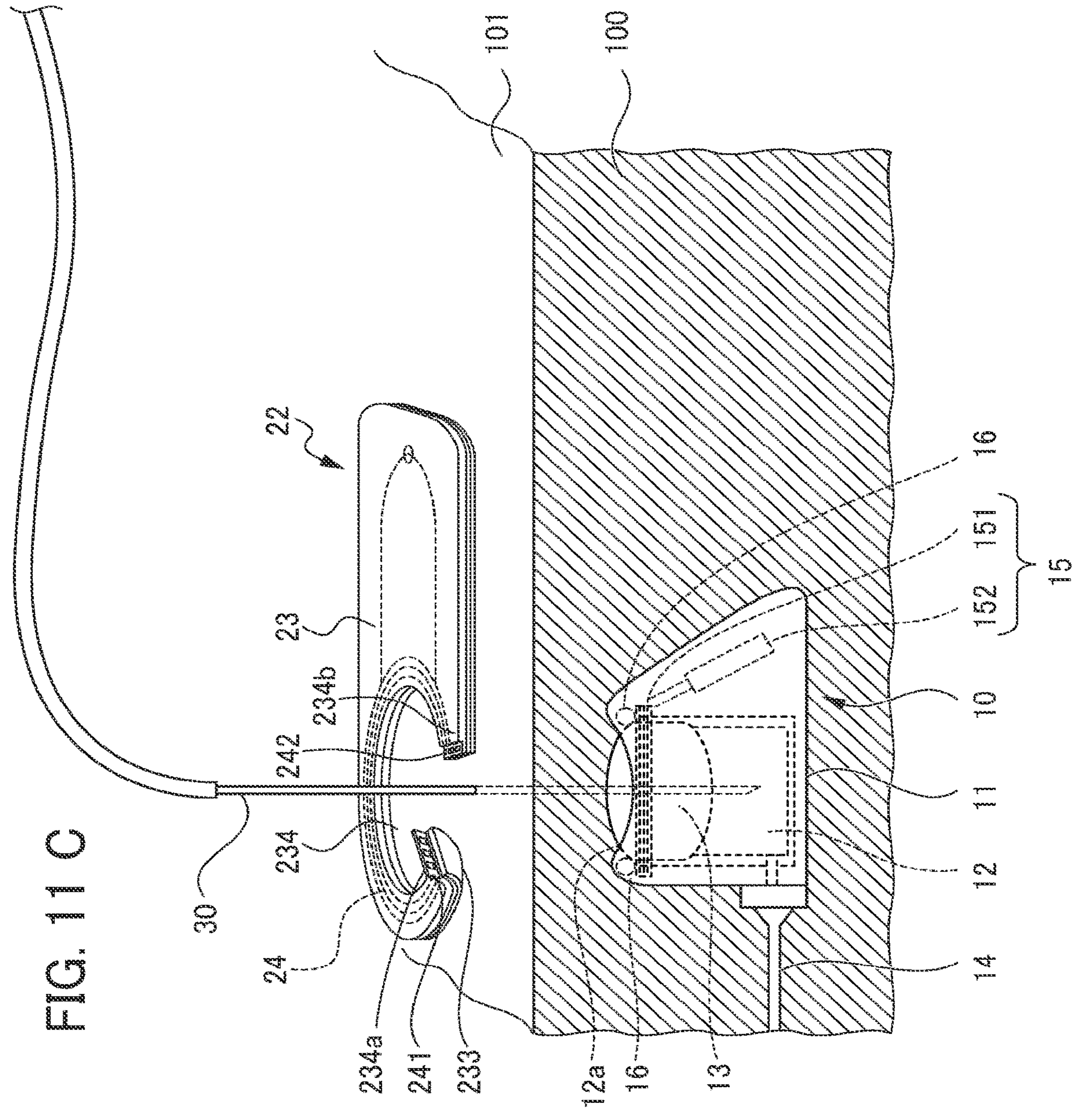
FIG. 11C is a third schematic view illustrating a situation in which the drug solution is supplied into the living body using the medical device according to the first embodiment of the present disclosure.

Next, description is given regarding a procedure for using the medical device 1 to supply a drug solution into the body of the living subject 100. FIG. 11A is a first schematic view illustrating a state before an injection needle 30 is inserted into the body surface 101. FIG. 11B is a second schematic view illustrating a state in which the injection needle 30 has been inserted into the soft section 13. FIG. 11C is a third schematic view illustrating a situation in which the power transmission section 22 is removed from the body surface 101.

As illustrated in FIG. 11A, a user affixes the power transmission section 22 to the body surface 101 through the adhesive section 233 so that the hole 234 in the power transmission section 22 is positioned above the medical appliance 10 implanted inside the body of the living subject 100. The user presses on the input section 213 on the power supply device 20, whereby electric power is supplied from the power source section 212 in the case section 21 to the power transmission coil 24 in the power transmission section 22. At this time, the power transmission coil 24 generates magnetic flux using the electric power supplied from the power source section 212 via the first connection section 211 and the second connection section 25.

In a case where the relative positional relationship between the medical appliance 10 and the power supply device 20 is within a predetermined range, induced electromotive force is generated from the power reception coil 151 due to the magnetic flux generated from the power transmission coil 24. The power reception circuit 152 receives electric power generated from the power reception coil 151, and outputs electric power to the light-emitting sections 16. In other words, electric power is supplied from the power supply device 20 to the medical appliance 10 in accordance with electromagnetic-induction-type non-contact supply of power. As a result, the light L is irradiated onto the top surface of the soft section 13 from a plurality of the light-emitting sections 16, as illustrated in FIG. 11A.

Next, as illustrated in FIG. 11B, the user inserts the injection needle 30, from an infusion device (illustration omitted) that holds a drug solution, into the soft section 13 which is positioned below the body surface 101. Specifically, the injection needle 30 is inserted into the center of four points on the body surface 101 which are illuminated by the light L emitted from each light-emitting section 16. Because it is possible to puncture the body surface while using the light L from the light-emitting sections 16 as a marker, it is possible to easily inject the drug solution into the drug solution container 12. In addition, because it is possible to affix the power supply device 20 to the body surface 101 through the adhesive section 233, the user can use both hands to perform a puncturing operation. Accordingly, it is possible to more easily supply the drug solution to the medical appliance 10 which is implanted inside the body of the living subject 100.

In this way, in the present embodiment, the light-emitting sections 16 are caused to emit light by the electric power supplied to the power reception coil 151 from the power transmission coil 24 using non-contact supply of power, and the position of the soft section 13 is notified to the user by this light. The user can grasp the position of the soft section 13 by using this notifying light as a guide.

In addition, when the injection needle 30 is inserted into the soft section 13, the user presses the input section 213 on the power supply device 20 to thereby cause the supply of electric power from the power source section 212 to the power transmission coil 24 to stop. The user then releases the connection between the first connection section 211 and the second connection section 25, and separates the case section 21 from the power transmission section 22.

As illustrated in FIG. 11C, when the user separates the connectors 241 and the connectors 242 to thereby release the ring-shaped state of the power transmission coil 24, the first connection end section 234*a* and the second connection end section 234*b* of the support body 23 are separated. A gap produced by releasing the ring-shaped state of the power transmission coil 24 is used to remove the power transmission section 22 from the body surface 101 while taking care to avoid coming into contact with the injection needle 30, which is in a state of puncturing the body surface 101, and the support body 23.

After the power transmission section 22 is removed from the body surface 101, the user starts injecting the drug solution into the medical appliance 10 from the infusion device.

In the first embodiment, the power supply device 20 is provided with the power transmission coil 24 that supplies electric power in a non-contact manner from outside the body via the power reception coil 151 in the intracorporeal implant-type medical appliance 10 which is injected with a drug solution from outside the body, the support body 23 that supports the power transmission coil 24, and the adhesive section 233 formed on the body surface 101 side of the support body 23. As a result, because it is possible to affix the power supply device 20 to the body surface 101 through the adhesive section 233, the user can use both hands to perform a puncturing operation. Accordingly, it is possible to easily perform a puncturing operation while supplying power to the medical appliance 10.

In addition, in the first embodiment, the elastic deformation section 232, which can deform and is disposed between the support body 23 and the adhesive section 233, is also provided. As a result, by using the elastic deformation section 232, it is possible to realize superior ability to follow unevenness on the body surface 101 of the living subject 100.

In the first embodiment, the adhesive force of the adhesive section 233 is typically 0.9 N/cm to 7.7 N/cm. As a result, because the adhesive force is within the range of 0.9 N/cm to 7.7 N/cm, it is possible to more reliably affix the power transmission section 22 to the body surface 101, and it is possible to easily remove the power transmission section 22 from the body surface 101.

In addition, in the first embodiment, the support body 23 and the adhesive section 233 have been subjected to sterilization treatment. As a result, it is possible to ensure cleanliness when performing puncturing because the adhesive section 233 which comes into contact with the body surface 101 and the support body 23 which is positioned near a puncturing site have been subjected to sterilization treatment.

In addition, in the first embodiment, the support body 23 has the hole 234 through which the injection needle 30 for injecting the drug solution can be inserted, and the power transmission coil 24 is disposed in a ring shape so as to surround the hole 234. As a result, because the power transmission coil 24 is disposed so as to surround the hole 234 through which the injection needle 30 can be inserted, supply of power is performed in a state where the medical appliance 10 is positioned inside the hole 234 in the plan view, whereby it is possible to more reliably transmit the magnetic flux generated from the power transmission coil 24 to the medical appliance 10. Accordingly, it is possible to realize higher power supply efficiency.

In addition, in the present embodiment, the power transmission coil 24 is configured such that it is possible to use the connectors 241 and 242 to release the ring-shaped state. As a result, it is possible to easily remove the power supply device 20 from the body surface 101 by releasing the ring-shaped state of the power transmission coil 24, even in a state where the injection needle 30 from an infusion device, etc. has been inserted into the soft section 13 through the hole 234 surrounded by the power transmission coil 24. As a result, it is possible to realize high power supply efficiency. By removing the power supply device 20 from the body surface 101 after a puncturing operation, it is also possible to reduce the load on the living subject 100 when the drug solution is being injected.

In the first embodiment, the diameter of the hole 234 in the support body 23 is at least 5 cm. As a result, even in the case where the power transmission section 22 has been affixed to the body surface 101 such that the soft section 13 is positioned inside the hole 234 in the plan view, it is possible to ensure space for the user to use their hand to hold the body surface so that the medical appliance 10 does not move when the user performs a puncturing operation. In the case where puncturing is performed such that the injection needle 30 passes through the hole 234 near the center of the hole 234, it is possible to provide a sufficient interval between the injection needle 30 and the power transmission section 22, and it is possible to ensure cleanliness around the injection needle 30.

In the first embodiment, the medical device 1 is provided with the power supply device 20 and the intracorporeal implant-type medical appliance 10. The medical appliance 10 is provided with the soft section 13 through which the injection needle 30 for injecting the drug solution is inserted, the drug solution container 12 which has the opening 12*a* occluded by the soft section 13 and receives the drug solution injected from the injection needle 30, and the power reception section 15 which can use the power reception coil 151 to receive, in a non-contact manner, power supplied from the power transmission coil 24 in the power supply device 20. As a result, because it is possible to use the adhesive section 233 to affix the power supply device 20 to the living subject 100, it is possible for the user to use both hands to insert the injection needle 30 into the soft section 13 while power is being supplied to the power reception section 15 from the power supply device 20. Accordingly, it is possible to easily perform a puncturing operation while supplying power to the medical appliance 10.

In the first embodiment, the medical appliance 10 is also provided with the light-emitting sections 16 that emit light using the electric power received by the power reception section 15. As a result, because the light L from the light-emitting sections 16 is emitted in accordance with the power supplied from the power supply device 20, it is possible to easily specify a location on the body surface 101 to be punctured by the injection needle 30.

In the first embodiment, the diameter of the hole 234 in the power supply device 20 is greater than the outer diameter of the soft section 13, and the radius of the hole 234 is greater than the distance between the light-emitting sections 16 and the center of the soft section 13 in the plan view. As a result, even in the case where the power transmission section 22 has been affixed to the body surface 101 such that the soft section 13 is positioned inside the hole 234 in the plan view, if the center of the hole 234 matches the center of the soft section 13 in the plan view, the light-emitting sections 16 will be positioned inside of the hole 234, and it is possible to more reliably visually recognize the light L emitted from the light-emitting sections 16.

Second Embodiment

Next, description is given regarding a second embodiment according to the present disclosure, while invoking the description of the first embodiment described above. Note that, in the following description, the same reference symbols are applied to components that are the same as those in the first embodiment described above, description of these components is omitted or simplified, with description primarily given for differences.

In the first embodiment described above, the hole 234 is provided in the center of the power transmission coil 24 in the power transmission section 22, but there is no limitation to this, and the shape of the power transmission section can be changed as appropriate.

Figure 12:
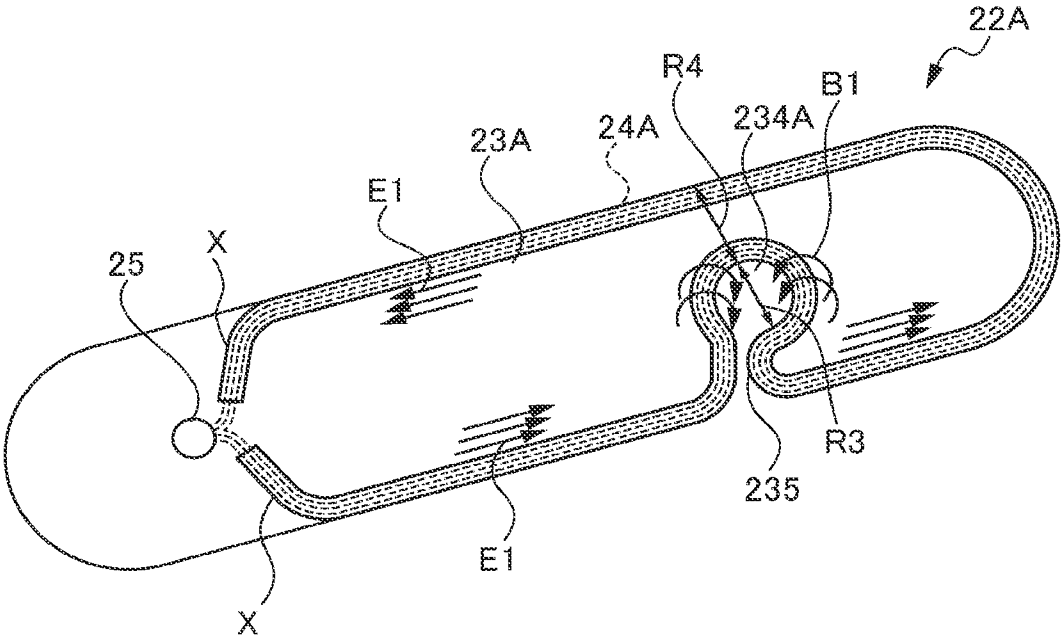
FIG. 12 is a plan view illustrating a power transmission section according to a second embodiment of the present disclosure.

FIG. 12 is a schematic view illustrating an approximate configuration of a power transmission section 22A according to the second embodiment. The power transmission section 22A has a support body 23A, the adhesive section 233, the elastic deformation section 232, a power transmission coil 24A, and the second connection section 25. The power transmission section 22A primarily differs from the power transmission section 22 in the configuration of the support body 23A and the power transmission coil 24A.

The support body 23A has a long and narrow plate shape. Both ends of the support body 23A in the longitudinal direction are formed as arc shapes. The support body 23A has, on one side in the longitudinal direction thereof, a cutout section 235 which has been cut out so that an injection needle can be inserted.

The cutout section 235 is cut out from near the approximate center in the width direction of the support body 23A towards an outer edge thereof. In the present embodiment, the cutout section 235 is configured by including an approximately circular opening 235*a* in a plan view, and a path 235*b* formed from the opening 235*a* to the outer edge of the support body 23A.

The power transmission coil 24A is formed in alignment with the shape of the cutout section 235. The power transmission coil 24A is disposed on the support body 23A so that cancellation of reverse-direction magnetic flux B1 due to a current E1 does not occur, and so that the flow of the current E1 is separated from an opposing portion.

Specifically, a portion where the cutout section 235 is formed, in particular, may be formed with a width R4 of the support body 23A being equal to or greater than a diameter R3 of the opening 235*a* (R4≥R3). In addition, as illustrated in FIG. 12, it is desirable for a portion of the power transmission coil 24A that is not formed near the cutout section 235 to be covered by a sheet X having electrical conductivity. Because the sheet X having electrical conductivity accomplishes the function of a shield, it is possible to shield the portion of the power transmission coil 24A that is not formed near the cutout section 235 from radiating a magnetic field externally, and it is possible prevent interaction between this portion and the power reception coil 151. Note that, for example, a metal sheet can be considered for the sheet X which has electrical conductivity.

In the second embodiment, the support body 23A has the cutout section 235 which is cut out to enable an injection needle for injecting a drug solution to be inserted, and the power transmission coil 24A is formed in alignment with the shape of the cutout section 235. As a result, because the cutout section 235 which enables an injection needle to be inserted is formed in the support body 23A, it is possible to easily remove the power transmission section 22A from the body surface 101 of the living subject 100 even in a state where an injection needle from an infusion device, etc. has been inserted into the soft section 13 through the cutout section 235. In addition, because the support body 23A and the power transmission coil 24A can be removed from the body surface 101 without deforming the support body 23A or the power transmission coil 24A, it is possible to repeatedly use the power transmission section 22A, and it is possible to reduce costs.

Third Embodiment

Next, description is given regarding a third embodiment according to the present disclosure, while invoking the description of the first embodiment described above. Note that, in the following description, the same reference symbols are applied to components that are the same as those in the first embodiment described above, description of these components is omitted or simplified, with description primarily given for differences.

Figure 13:
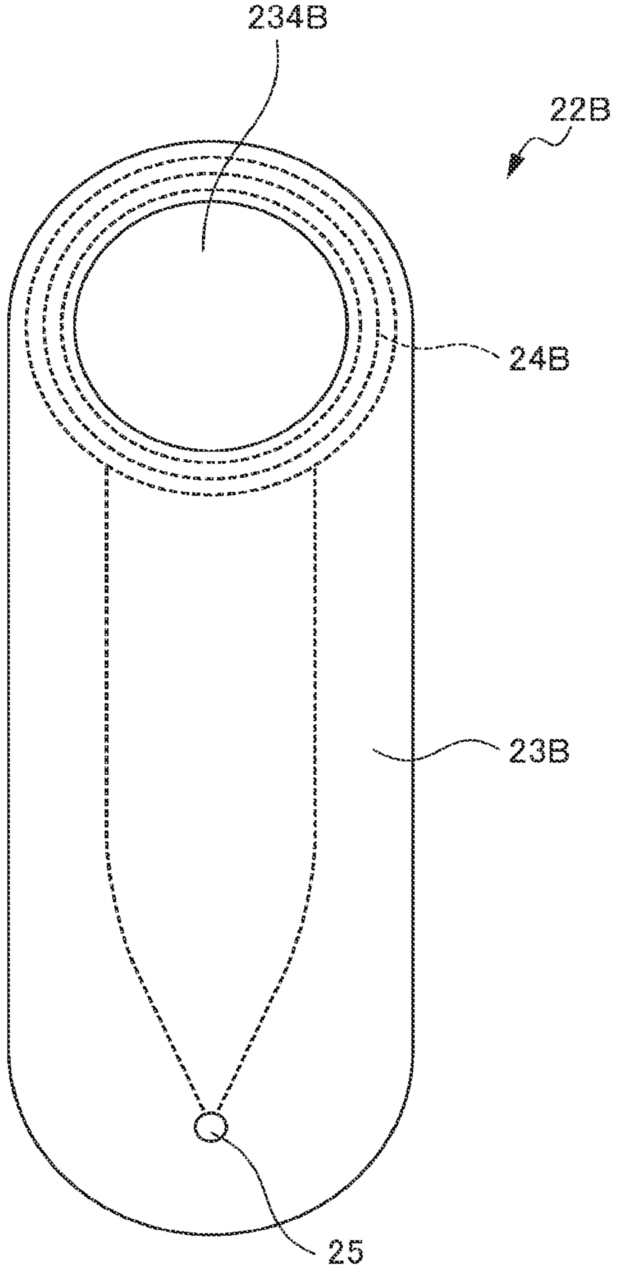
FIG. 13 is a plan view illustrating a power transmission section according to a third embodiment of the present disclosure.

FIG. 13 is a plan view illustrating a power transmission section 22B according to the third embodiment. The power transmission section 22B has a support body 23B, the adhesive section 233, the elastic deformation section 232, a power transmission coil 24B, and the second connection section 25. The power transmission section 22B primarily differs from the power transmission section 22 in the configuration of the support body 23B and the power transmission coil 24B.

The support body 23B has a long and narrow plate shape. Both ends of the support body 23B in the longitudinal direction are formed as arc shapes. The support body 23B is realized using non-woven fabric, for example. The support body 23B is formed using two pieces of non-woven fabric that interpose the power transmission coil 24B and the second connection section 25 therebetween.

A hole 234B, which is an opening through which an injection needle can be inserted, is formed at one side of the support body 23B in the longitudinal direction. The hole 234 in the support body 23 according to the first embodiment is configured such that the ring-shaped state is released by the first connection end section 234*a* and the second connection end section 234*b*, which overlap each other, being separated from each other. However, the support body 23B has a contiguous structure without a discontinuity at the periphery of the hole 234B.

The power transmission coil 24B is a planar coil provided in a ring shape at the periphery of the hole 234B. The power transmission coil 24B generates magnetic flux in response to electric power inputted from the case section 21 via the second connection section 25. The power transmission coil 24 according to the first embodiment is configured such that the ring-shaped state can be released using the connectors 241 and 242, but the power transmission coil 24B has a structure that lacks the connectors 241 and 242 and thus the ring-shaped state thereof is not released.

In addition, the power transmission section 22B is configured such that it is possible to transmit power to the power reception section 15 in the medical appliance 10 even if the distance between the center of the soft section 13 and the power transmission section 22B in the plan view becomes 2.5 cm or more.

Figure 14:
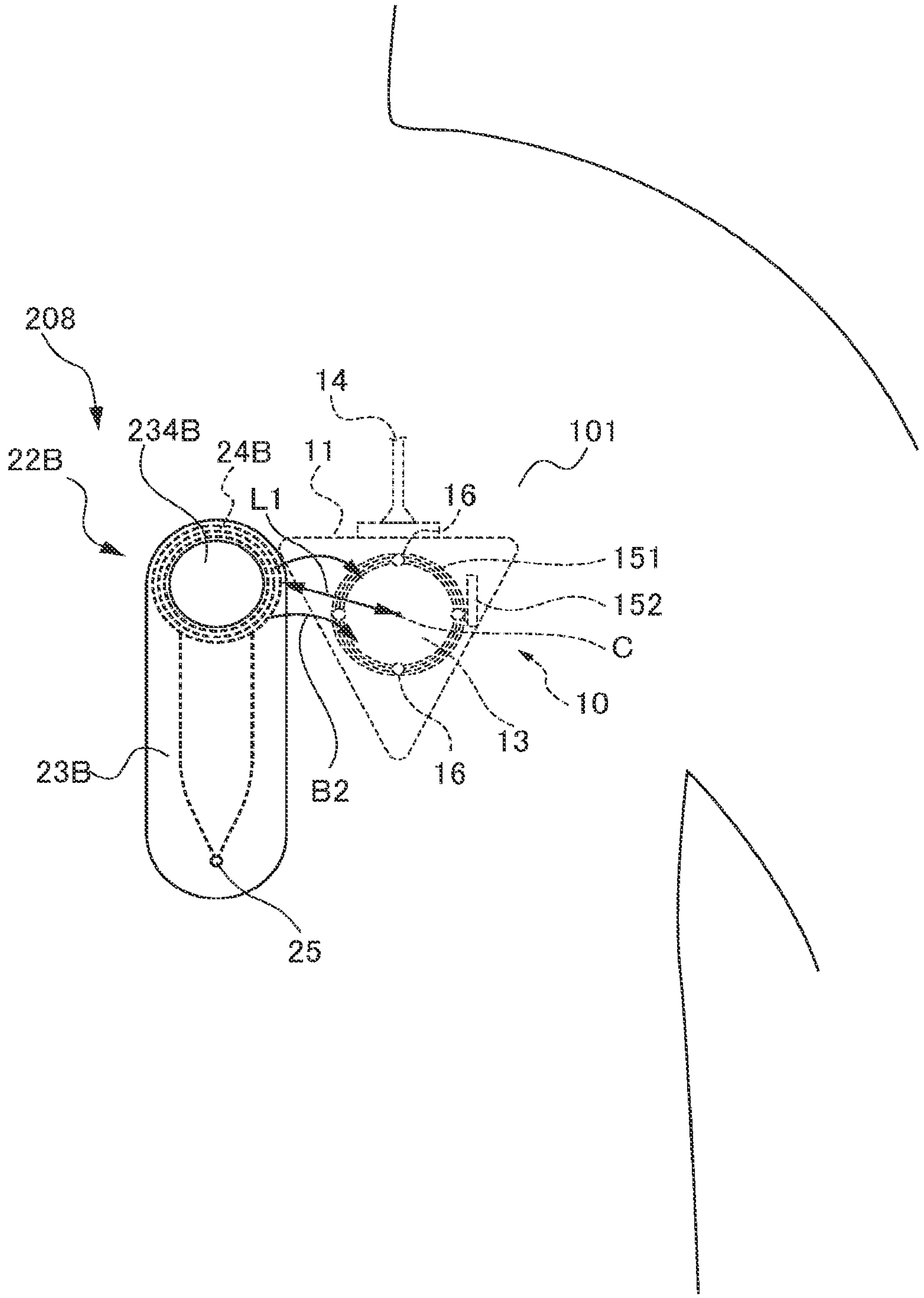
FIG. 14 is a schematic view illustrating a state in which the power transmission section according to the third embodiment of the present disclosure has been affixed to a living subject.

Next, description is given for an example of using a power supply device 20B which has the power transmission section 22B in order to supply power to the medical appliance 10 which is implanted inside the body of the living subject 100. FIG. 14 is a schematic view illustrating a state in which the power transmission section 22B is attached to the living subject. Note that FIG. 14 omits illustration of the case section 21 in the power supply device 20B.

As illustrated in FIG. 14, a user affixes, through the adhesive section 233, the power transmission section 22B to the body surface 101 near the medical appliance 10 which is implanted inside the body of the living subject 100. In FIG. 14, the support body 23B is disposed such that the soft section 13 is positioned outside of the hole 234B in a plan view.

When the user presses the input section 213 to cause magnetic flux B2 to be generated from the power transmission coil 24B, induced electromotive force is generated from the power reception coil 151, and the top surface of the soft section 13 is irradiated with light from the light-emitting sections 16. The user then inserts the injection needle into the soft section 13 positioned below the body surface 101 while using the light from the light-emitting sections 16 as a marker.

In an example of using the power supply device 20B in FIGS. 11A to 11C in the first embodiment, it was necessary to perform puncturing by inserting the injection needle 30 into the hole 234 because the power transmission section 22 was affixed to the body surface 101 such that the hole 234 surrounds the soft section 13 in the plan view. In contrast to this, in the example of use in FIG. 14, because the injection needle 30 in a state of having been inserted into the soft section 13 is positioned outside of the hole 234B in the plan view, it is possible to easily remove the power transmission section 22B from the body surface 101 without coming into contact with the injection needle 30.

Fourth Embodiment

Next, description is given regarding a fourth embodiment according to the present disclosure, while invoking the description of the first embodiment described above. Note that, in the following description, the same reference symbols are applied to components that are the same as those in the first embodiment described above, description of these components is omitted or simplified, with description primarily given for differences.

Figure 15:
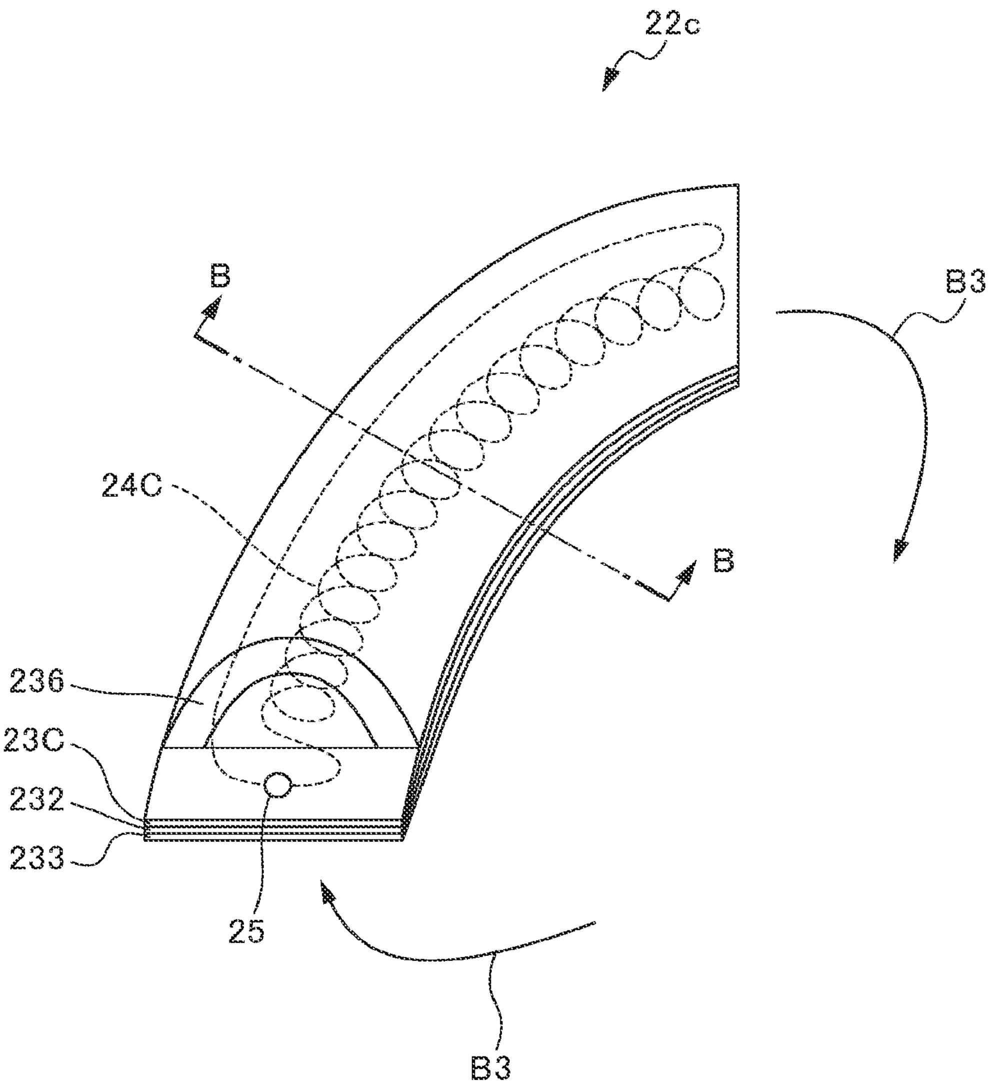
FIG. 15 is a plan view illustrating a power transmission section according to a fourth embodiment of the present disclosure.

FIG. 15 is a perspective view illustrating a power transmission section 22C according to the fourth embodiment.

Figure 16:
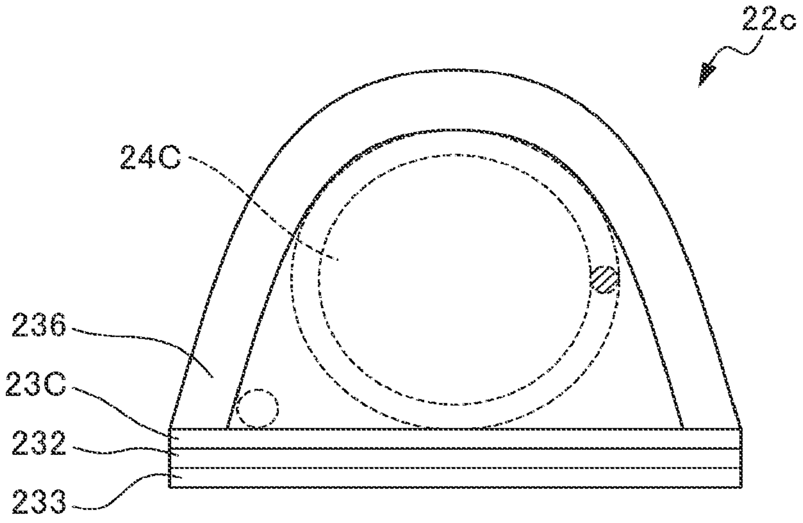
FIG. 16 is a cross-sectional view illustrating the power transmission section according to the fourth embodiment of the present disclosure.
Figure 17:
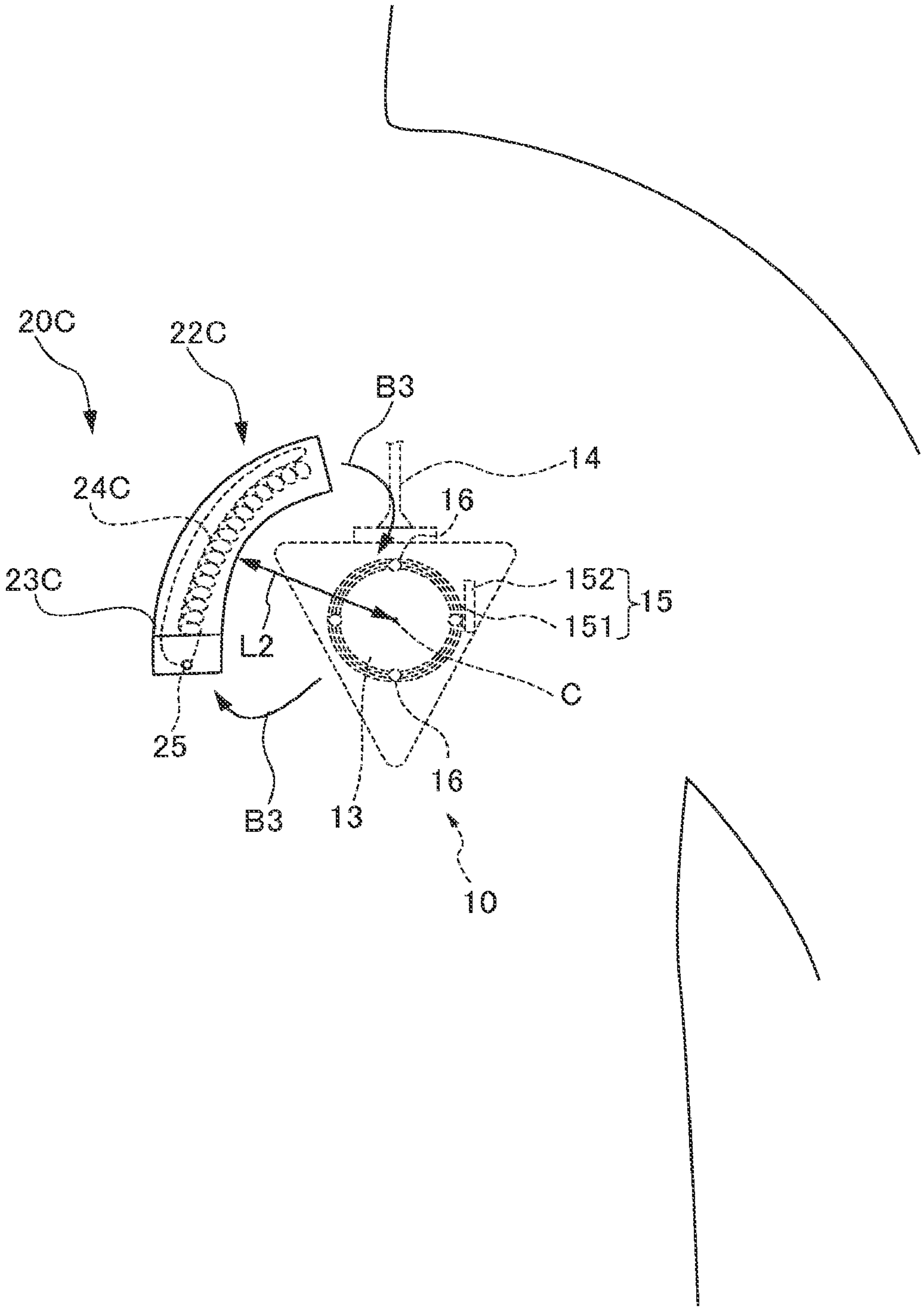
FIG. 17 is a schematic view illustrating a state in which the power transmission section according to the fourth embodiment of the present disclosure has been affixed to a living subject.

FIG. 16 is a cross-sectional view that cuts the power transmission section 22C along the B-B line illustrated in FIG. 15. FIG. 17 is a schematic view illustrating a state in which the power transmission section 22C is attached to a living subject. Note that FIG. 17 omits illustration of the case section 21 in a power supply device 20C.

The power transmission section 22C has a support body 23C, the adhesive section 233, the elastic deformation section 232, a cover section 236, a power transmission coil 24C, and the second connection section 25. The power transmission section 22C primarily differs from the power transmission section 22 in the configuration of the support body 23C and the power transmission coil 24C, and in that the power transmission section 22C has the cover section 236.

As illustrated in FIG. 15, the support body 23C is a plate-shaped member that is curved with an arc shape in a plan view. The power transmission coil 24C and the second connection section 25 are disposed on the top surface of the support body 23C (the top surface being the surface on the side opposite to the body surface 101).

The cover section 236 covers the top and sides of the power transmission coil 24C, which is disposed on the top surface of the support body 23C.

The power transmission coil 24C is a solenoid coil formed into a three-dimensional spiral. The power transmission coil 24C is formed into a cylindrical shape as a whole. The power transmission coil 24C generates magnetic flux B3 in response to electric power inputted from the case section 21 via the second connection section 25.

The power transmission coil 24C is formed on the top surface of the support body 23C so as to extend in an arc shape in alignment with the shape of the support body 23C. The power transmission coil 24C is disposed on the support body 23C such that the axial direction of the power transmission coil 24C is approximately parallel to the adhesive section 233.

As illustrated in FIG. 15, the magnetic flux B3 generated from the power transmission coil 24C is outputted from one end side of the power transmission coil 24C in the axial direction, and subsequently flows through the inner peripheral side of the support body 23C toward the other end side in the axial direction, and flows so as to enter within the power transmission coil 24C from the other end side in the axial direction.

In addition, the power transmission section 22C is configured such that it is possible to transmit power to the power reception section 15 in the medical appliance 10 by causing the magnetic flux B3 to be generated, even if a distance D2 between a center C of the soft section 13 and the power transmission section 22C in the plan view becomes 2.5 cm or more. As a result, in a case where the injection needle 30 has been inserted into the center C of the soft section 13, it is possible to provide a sufficient interval between the injection needle 30 and the power transmission section 22C, and it is possible to ensure cleanliness around the injection needle 30.

Next, description is given for an example of using the power supply device 20C which has the power transmission section 22C in order to supply electric power to the medical appliance 10 which is implanted inside the body of the living subject 100.

As illustrated in FIG. 17, a user affixes, through the adhesive section 233, the power transmission section 22C to the body surface 101 near the medical appliance 10 which is implanted inside the body of the living subject 100. Specifically, as illustrated in FIG. 17, the power transmission section 22C is affixed so that the power reception section 15 is positioned on the inner peripheral side of the support body 23C in a plan view. At this time, an interval of at least 2.5 cm is opened between the center of the soft section 13 and the power transmission section 22C in a plan view, and the power transmission section 22C is affixed to a position at which it is possible to transmit power to the power reception section 15 in the medical appliance 10.

When the user presses the input section 213 to cause magnetic flux B3 to be generated from the power transmission coil 24C, induced electromotive force is generated from the power reception coil 151, and the top surface of the soft section 13 is irradiated with light from the light-emitting sections 16. The user then inserts the injection needle 30 into the soft section 13 positioned below the body surface 101 while using the light from the light-emitting sections 16 as a marker.

In the fourth embodiment, the power transmission coil 24C is formed into a three-dimensional spiral. As a result, it is possible to supply power to the medical appliance 10 from the power transmission section 22C without surrounding the periphery of the soft section 13 in the medical appliance 10 in the plan view. Accordingly, because an injection needle inserted into the soft section 13 is positioned outside of the power transmission section 22C, it is possible to easily remove the power transmission section 22C from the body surface 101 even in a state where the injection needle has been inserted into the soft section 13.

Fifth Embodiment

Next, description is given regarding a fifth embodiment according to the present disclosure, while invoking the description of the fourth embodiment described above. Note that, in the following description, the same reference symbols are applied to components that are the same as those in the fourth embodiment described above, description of these components is omitted or simplified, with description primarily given for differences.

Figure 18:
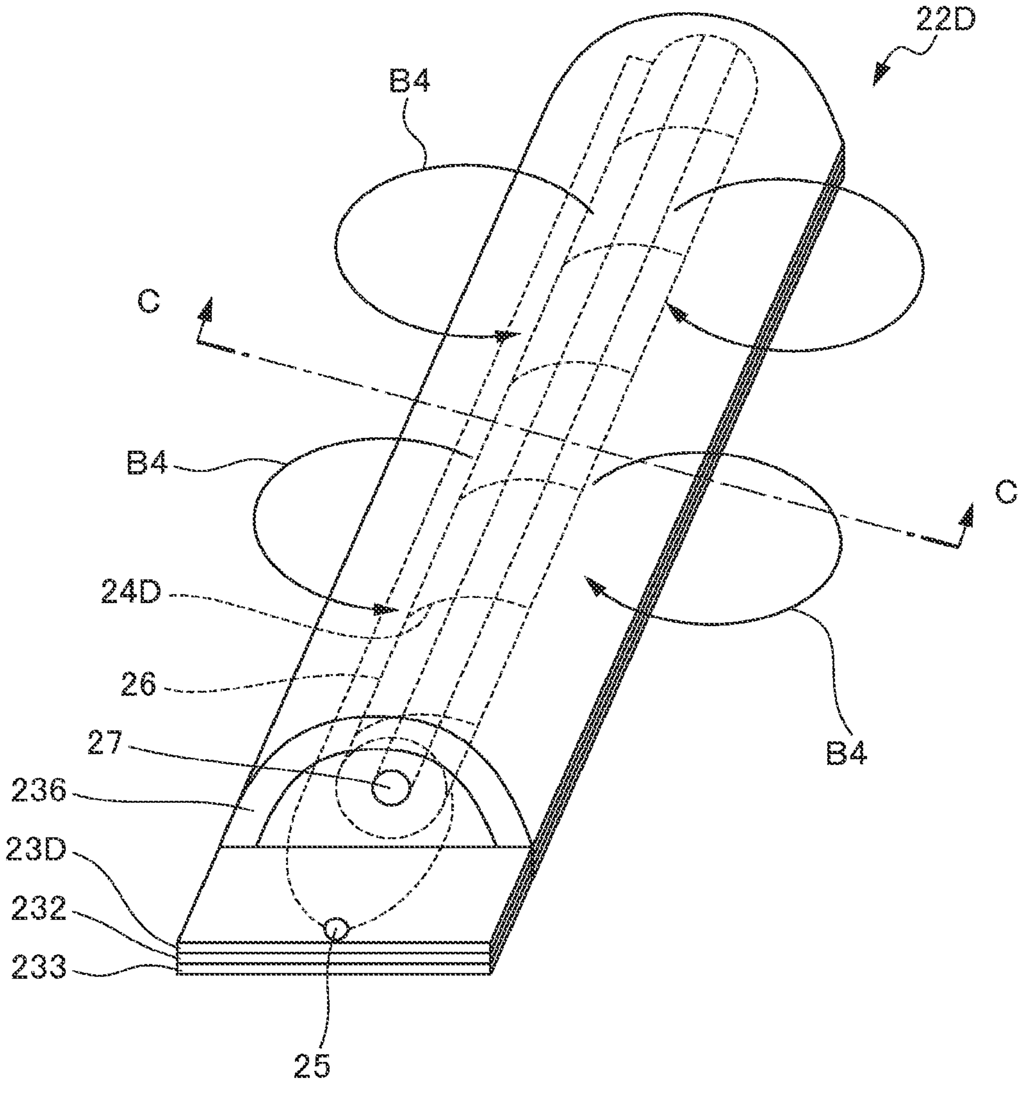
FIG. 18 is a perspective view illustrating a power transmission section according to a fifth embodiment of the present disclosure.
Figure 19:
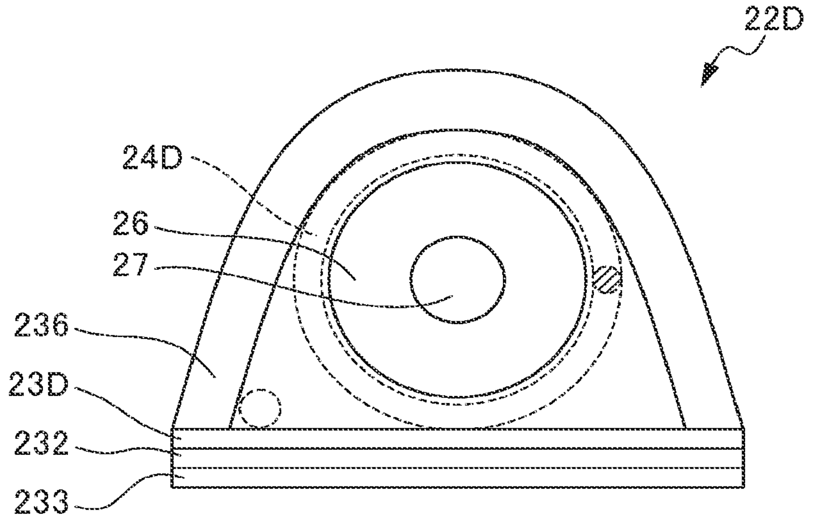
FIG. 19 is a cross-sectional view illustrating the power transmission section according to the fifth embodiment of the present disclosure.
Figure 20:
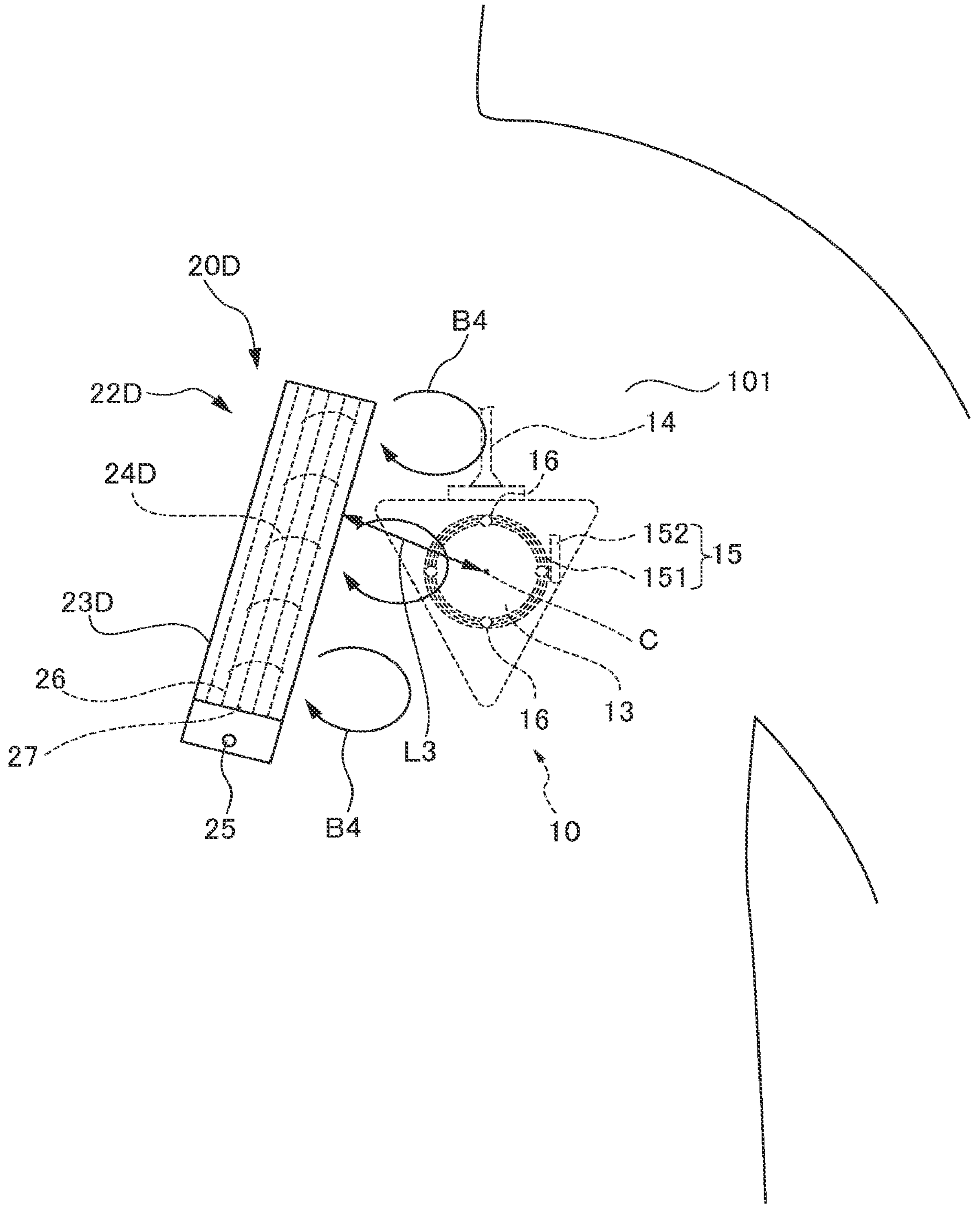
FIG. 20 is a schematic view illustrating a state in which the power transmission section according to the fifth embodiment of the present disclosure has been affixed to a living subject.

FIG. 18 is a perspective view illustrating a power transmission section 22D according to the fifth embodiment. FIG. 19 is a cross-sectional view resulting from cutting the power transmission section 22D along the C-C line illustrated in FIG. 18. FIG. 20 is a schematic view illustrating a state in which the power transmission section 22D is attached to a living subject. Note that FIG. 20 omits illustration of the case section 21 in a power supply device 20D.

The power transmission section 22D has a support body 23D, the adhesive section 233, the elastic deformation section 232, a cover section 236, a power transmission coil 24D, the second connection section 25, a tubular body 26, and a core material 27. The power transmission section 22D primarily differs from the power transmission section 22C in the shape of the support body 23D, the configuration of the power transmission coil 24D, and in that the power transmission coil 24D has the tubular body 26 and the core material 27.

As illustrated in FIG. 18, the support body 23D has a long and narrow plate shape. The support body 23C according to the fourth embodiment is formed into an arc shape in the plan view, but the support body 23D is linearly formed in the plan view. The power transmission coil 24D and the second connection section 25 are disposed on the top surface of the support body 23D (the top surface being the surface on the side opposite to the body surface 101).

The tubular body 26 is a member that has a cylindrical shape. Windings of the power transmission coil 24D are wound around the outer peripheral surface of the tubular body 26. The tubular body 26 is disposed along the longitudinal direction of the support body 23D.

The core material 27 is a magnetic body having an approximately circular columnar shape. As illustrated in FIG. 18, the core material 27 is positioned at the central axis of the tubular body 26 in the cross-sectional view, while also extending along the axial direction of the tubular body 26. The material of the core material 27 may be ferrite, for example.

The power transmission coil 24D is a helical coil that is wound around the tubular body 26 and is formed in a three-dimensional spiral shape. The power transmission coil 24D is formed into a cylindrical shape as a whole. The power transmission coil 24D generates magnetic flux B4 in response to electric power inputted from the case section 21 via the second connection section 25.

The power transmission coil 24D is more sparsely wound than the power transmission coil 24C, and the core material 27 which is a magnetic body is disposed at the central axis of the power transmission coil 24D. By virtue of the power transmission section 22D having such a configuration, it is possible to generate the magnetic flux B4 in directions that turn around the outside of the power transmission section 22D and are centered on the windings of the power transmission coil 24D, as illustrated in FIG. 18.

In addition, the power transmission section 22D is configured such that it is possible to transmit power to the power reception section 15 in the medical appliance 10 by causing the magnetic flux B4 to be generated, even if the distance between the center of the soft section 13 and the power transmission section 22D in the plan view becomes 2.5 cm or more.

Next, description is given for an example of using a power supply device 20D which has the power transmission section 22D in order to supply power to the medical appliance 10 which is implanted inside the body of the living subject 100.

As illustrated in FIG. 20, a user affixes, through the adhesive section 233, the power transmission section 22D to the body surface 101 near the medical appliance 10 which is implanted inside the body of the living subject 100. Specifically, an interval of at least 2.5 cm is opened between the center C of the soft section 13 and the power transmission section 22D in a plan view, and the power transmission section 22D is affixed to a position at which it is possible to transmit electric power to the power reception section 15 in the medical appliance 10.

When the user presses the input section 213 to cause magnetic flux B4 to be generated from the power transmission coil 24D, induced electromotive force is generated from the power reception coil 151, and the top surface of the soft section 13 is irradiated with light from the light-emitting sections 16. The user then inserts the injection needle 30 into the soft section 13 positioned below the body surface 101 while using the light from the light-emitting sections 16 as a marker.

In the fifth embodiment, because an injection needle inserted into the soft section 13 is positioned outside of the power transmission section 22D, it is possible to easily remove the power transmission section 22D from the body surface 101 even in a case where the injection needle 30 has been inserted into the soft section 13.

Other Embodiments

In the above-described first to fifth embodiments according to the present disclosure, in the case where the relative positional relationship between a medical appliance and a power supply device is in a predetermined state, magnetic induction is used to cause the light-emitting sections 16 to emit light to thereby notify the position of the soft section 13 to a user, but there is no limitation to this and application is possible even in a case of using magnetic field resonance, radio wave reception, or electric field coupling.

In addition, in the above-described first to fifth embodiments according to the present disclosure, the power transmission section and the case section are given as separate bodies, but there is no limitation to this, and the power transmission section and the case section may be integral.

In addition, in the above-described first to fifth embodiments according to the present disclosure, electric power is supplied to the power transmission section by the power transmission section and the case section being electrically connected, but there is no limitation to this, and electric power may be supplied from the case section to the power transmission section using wireless supply of power, for example.

In addition, in the above-described first to fifth embodiments according to the present disclosure, a power source section is provided in the case section, but there is no limitation to this, and a power source section may be provided in the power transmission section, for example. The power source section is configured by including a battery which serves as a power source, but it may be that a power cable is provided instead of the battery and electric power is obtained via the power cable, which is connected to an external power source.

In addition, it is possible to form various inventions by appropriately combining a plurality of components, which were disclosed by the medical device according to the above-described first to fifth embodiments according to the present disclosure. For example, any number of all of the components described by the medical device according to the above-described first to fifth embodiments of the present disclosure may be deleted. Furthermore, components described by the medical device according to the above-described first to fifth embodiments of the present disclosure may be combined, as appropriate.

In addition, for the medical device according to the above-described first to fifth embodiments of the present disclosure, "section" mentioned above can be interpreted as "means", "circuit", etc. For example, the control section can be interpreted as a control means or a control circuit.

In addition, a program caused to be executed by the medical device according to the first to fifth embodiments of the present disclosure is provided, as file data in a format that can be installed or in a format that can be executed, by being recorded onto a computer-readable recording medium such as a CD-ROM, a floppy disk (FD), a CD-R, a Digital Versatile Disc (DVD), a USB medium, or a flash memory.

While some embodiments of the present application have been described in detail above based on the drawings, the embodiments are described by way of example. The present disclosure may be worked in various other modes after making various modifications and improvements based on knowledge held by a person skilled in the art, in addition to the aspects described in this specification.

EXPLANATION OF REFERENCE NUMERALS

10 Medical appliance
20 Power supply device
23 Support body
24 Power transmission coil
233 Adhesive section
101 Body surface

The invention claimed is:

1. A power supply device, comprising:
a power transmission coil configured to supply power in a non-contact manner from outside the body via a coil in an intracorporeal implant-type medical appliance configured to be injected with a drug solution from outside the body;
a support body configured to support the power transmission coil; and
an adhesive section formed on the support body, on a side of the support body that faces a body surface of a living subject, wherein
the support body has a hole through which an injection needle for injecting the drug solution can be inserted,
the power transmission coil is disposed so as to surround the hole,
the power transmission coil is provided with a first connector and a second connector between conductors of the power transmission coil, the first connector and the second connector being configured to be attached to and detached from each other,
the first connector and the second connector are connected to each other such that the power transmission coil is formed into a ring shape as a whole, and
the first connector and the second connector are separated from each other such that a state of being in the ring shape of the power transmission coil is released.

2. The power supply device according to claim 1, further comprising: an elastic deformation section disposed between the support body and the adhesive section, the elastic deformation section being deformable.

3. The power supply device according to claim 2, wherein the support body and the adhesive section have been subjected to sterilization treatment.

4. A medical device, comprising:
the power supply device according to claim 2; and
an intracorporeal implant-type medical appliance,
wherein the medical appliance is provided with
a soft section through which an injection needle for injecting a drug solution can be inserted,
a drug solution container having an opening occluded by the soft section and being configured to receive the drug solution injected from the injection needle, and
a power reception section configured to use a coil to receive, in a non-contact manner, power supplied from the power transmission coil in the power supply device.

5. The power supply device according to claim 1, wherein the support body and the adhesive section have been subjected to sterilization treatment.

6. A medical device, comprising:
the power supply device according to claim 5; and
an intracorporeal implant-type medical appliance,
wherein the medical appliance is provided with
a soft section through which an injection needle for injecting a drug solution can be inserted,
a drug solution container having an opening occluded by the soft section and being configured to receive the drug solution injected from the injection needle, and
a power reception section configured to use a coil to receive, in a non-contact manner, power supplied from the power transmission coil in the power supply device.

7. The power supply device according to claim 1, wherein the power transmission coil is provided with the first connector and the second connector between conductors that configure coils of the power transmission coil.

8. A medical device, comprising:
the power supply device according to claim 7; and
an intracorporeal implant-type medical appliance,
wherein the medical appliance is provided with
a soft section through which an injection needle for injecting a drug solution can be inserted,
a drug solution container having an opening occluded by the soft section and being configured to receive the drug solution injected from the injection needle,
a power reception section configured to use a coil to receive, in a non-contact manner, power supplied from the power transmission coil in the power supply device, and
a light-emitting section configured to emit light,
wherein a diameter of the hole in the power supply device is greater than an outer diameter of the soft section, and a radius of the hole is greater than a distance between the center of the soft section and the light-emitting section in a plan view.

9. A medical device, comprising:
the power supply device according to claim 7; and
an intracorporeal implant-type medical appliance,
wherein the medical appliance is provided with
a soft section through which an injection needle for injecting a drug solution can be inserted, a drug solution container having an opening occluded by the soft section and being configured to receive the drug solution injected from the injection needle, and a power reception section configured to use a coil to receive, in a non-contact manner, power supplied from the power transmission coil in the power supply device.

10. A medical device, comprising:

the power supply device according to claim 1; and an intracorporeal implant-type medical appliance, wherein the medical appliance is provided with a soft section through which an injection needle for injecting a drug solution can be inserted, a drug solution container having an opening occluded by the soft section and being configured to receive the drug solution injected from the injection needle, and a power reception section configured to use a coil to receive, in a non-contact manner, power supplied from the power transmission coil in the power supply device.

11. The medical device according to claim 10, wherein the medical appliance is further provided with a light-emitting section configured to emit light.

12. A medical device, comprising:

the power supply device according to claim 1; and an intracorporeal implant-type medical appliance, wherein the medical appliance is provided with a soft section through which an injection needle for injecting a drug solution can be inserted, a drug solution container having an opening occluded by the soft section and being configured to receive the drug solution injected from the injection needle, a power reception section configured to use a coil to receive, in a non-contact manner, power supplied from the power transmission coil in the power supply device, and a light-emitting section configured to emit light, wherein a diameter of the hole in the power supply device is greater than an outer diameter of the soft section, and a radius of the hole is greater than a distance between the center of the soft section and the light-emitting section in a plan view.

13. A medical device, comprising:

the power supply device according to claim 1; and an intracorporeal implant-type medical appliance, wherein the medical appliance is provided with a soft section through which an injection needle for injecting a drug solution can be inserted, a drug solution container having an opening occluded by the soft section and being configured to receive the drug solution injected from the injection needle, and a power reception section configured to use a coil to receive, in a non-contact manner, power supplied from the power transmission coil in the power supply device.

* * * * *